(12) United States Patent
Yamashita et al.

(10) Patent No.: US 10,011,677 B2
(45) Date of Patent: Jul. 3, 2018

(54) POLYCARBODIIMIDE COMPOSITION, METHOD FOR PRODUCING POLYCARBODIIMIDE COMPOSITION, AQUEOUS DISPERSION COMPOSITION, SOLUTION COMPOSITION, RESIN COMPOSITION, AND CURED RESIN

(71) Applicant: MITSUI CHEMICALS, INC., Tokyo (JP)

(72) Inventors: Tatsuya Yamashita, Ichihara (JP); Toshihiko Nakagawa, Ichihara (JP); Shinji Kiyono, Kimitsu (JP); Aya Nakagawa, Sodegaura (JP); Hirokazu Morita, Chiba (JP); Shigeru Mio, Chiba (JP); Satoshi Yamasaki, Chiba (JP); Kazuki Sakata, Chiba (JP)

(73) Assignee: MITSUI CHEMICALS, INC., Tokyo (JP)

( * ) Notice: Subject to any disclaimer, the term of this patent is extended or adjusted under 35 U.S.C. 154(b) by 0 days.

(21) Appl. No.: 15/576,204

(22) PCT Filed: Jan. 5, 2017

(86) PCT No.: PCT/JP2017/000121
§ 371 (c)(1),
(2) Date: Nov. 21, 2017

(87) PCT Pub. No.: WO2017/119443
PCT Pub. Date: Jul. 13, 2017

(65) Prior Publication Data
US 2018/0148533 A1 May 31, 2018

(30) Foreign Application Priority Data

Jan. 5, 2016 (JP) ................. 2016-000418
Aug. 19, 2016 (JP) ................. 2016-161503

(51) Int. Cl.
*C08G 18/09* (2006.01)
*C07C 267/00* (2006.01)
*C07B 61/00* (2006.01)
*C08G 18/73* (2006.01)
*C08G 18/83* (2006.01)
*C08G 18/30* (2006.01)
*C08G 18/12* (2006.01)
*C08G 18/48* (2006.01)

(52) U.S. Cl.
CPC .......... *C08G 18/095* (2013.01); *C08G 18/12* (2013.01); *C08G 18/30* (2013.01); *C08G 18/4862* (2013.01); *C08G 18/73* (2013.01); *C08G 18/833* (2013.01)

(58) Field of Classification Search
None
See application file for complete search history.

(56) References Cited

U.S. PATENT DOCUMENTS 2,853,473 A * 9/1958 Campbell ........... C08G 18/025
106/122
6,124,398 A 9/2000 Horie

FOREIGN PATENT DOCUMENTS

| JP | 10316930 | A2 | 12/1998 |
|----|----------|-----|---------|
| JP | 2005015734 | A2 | 1/2005 |
| JP | 3630527 | B2 | 3/2005 |
| JP | 3715464 | B2 | 11/2005 |
| JP | 2006070186 | A2 | 3/2006 |
| JP | 2010159339 | A2 | 7/2010 |
| JP | 2014141594 | A1 | 8/2014 |
| JP | 2015199917 | A2 | 11/2015 |
| WO | 2010098027 | A1 | 9/2010 |

OTHER PUBLICATIONS

International Search Report dated Mar. 28, 2017 filed in PCT/JP2017/000121.

* cited by examiner

*Primary Examiner* — Christopher M Rodd
(74) *Attorney, Agent, or Firm* — Rankin, Hill & Clark LLP

(57) ABSTRACT

A polycarbodiimide composition is a reaction product of polyisocyanate having a primary isocyanate group and alcohols, wherein in an infrared absorption spectrum, the intensity ratio ($IR_{CI}/IR_{UI+U}$) of absorbance $IR_{CI}$ at or near 2120 $cm^{-1}$ due to stretching vibration of the carbodiimide group relative to absorbance $IR_{UI+U}$ at or near 1720 $cm^{-1}$ due to stretching vibration of the uretonimine group and urethane group is 1.5 or more and 4.5 or less.

13 Claims, 2 Drawing Sheets

POLYCARBODIIMIDE COMPOSITION, METHOD FOR PRODUCING POLYCARBODIIMIDE COMPOSITION, AQUEOUS DISPERSION COMPOSITION, SOLUTION COMPOSITION, RESIN COMPOSITION, AND CURED RESIN

TECHNICAL FIELD

The present invention relates to a polycarbodiimide composition, a method for producing a polycarbodiimide composition, an aqueous dispersion composition, a solution composition, a resin composition, and a cured resin.

BACKGROUND ART

Conventionally, in the field of paint, adhesive, and coating, a resin composition including a base component and a curing agent is known, and for the curing agent, for example, a carbodiimide curing agent is known.

To be more specific, for the carbodiimide curing agent, for example, Patent Document 1 (Synthesis Example 82) below has proposed a polycarbodiimide composition produced by reaction of 673 g of hexamethylenediisocyanate (HDI), and 800 g of polyethylene glycol monomethylether having an average molecular weight of 400 at 120° C. for 1 hour, and by further adding 13.5 g of a carbodiimide-formation catalyst (3-methyl-1-phenyl-2-phospholene-1-oxide), and further allowing the mixture to react at 185° C. for 5 hours.

By drying and curing such a resin composition composed of a polycarbodiimide composition (curing agent) and a base component, a cured resin such as coating can be produced.

CITATION LIST

Patent Document

[Patent Document 1]
Japanese Unexamined Patent Publication No. Hei 10-316930

SUMMARY OF THE INVENTION

Problem to be Solved by the Invention

Meanwhile, for the resin composition, in view of improvement in production efficiency and workability, curing at a relatively low temperature (e.g., 80° C. or less) by relatively a short period of time (e.g., 10 minutes or less) (that is, low temperature-fast curing properties) are required.

However, when the polycarbodiimide composition described in Patent Document 1 is used, there are disadvantages in that low temperature-fast curing properties of the resin composition are insufficient, and the cured resin produced under conditions of relatively low temperature and relatively short period of time has insufficient physical properties (e.g., water resistance, chemical resistance properties).

An object of the present invention is to provide a polycarbodiimide composition having excellent low temperature-fast curing properties, a method for producing a polycarbodiimide composition, an aqueous dispersion composition and solution composition including the polycarbodiimide composition, a resin composition including the polycarbodiimide composition, and furthermore, a cured resin produced by curing the resin composition.

Means for Solving the Problem

The present invention [1] includes a polycarbodiimide composition that is a reaction product of polyisocyanate having a primary isocyanate group and alcohols, wherein the polycarbodiimide composition includes a carbodiimide group and a uretonimine group, and in an infrared absorption spectrum, the intensity ratio ($IR_{CI}/IR_{UI+U}$) of absorbance $IR_{CI}$ at or near 2120 $cm^{-1}$ due to stretching vibration of the carbodiimide group relative to absorbance $IR_{UI+U}$ at or near 1720 $cm^{-1}$ due to stretching vibration of the uretonimine group and urethane group is 1.5 or more and 4.5 or less.

The present invention [2] includes the polycarbodiimide composition of the above-described [1], wherein in the polycarbodiimide composition, the proportion of the uretonimine group relative to a total mol of the carbodiimide group and the uretonimine group is 1.5 mol % or more and 15 mol % or less.

The present invention [3] includes the polycarbodiimide composition of the above-described [1] or [2], wherein the equivalent ratio (NCO/OH) of the isocyanate group of the polyisocyanate relative to the hydroxyl group of the alcohols is more than 2 and 16 or less.

The present invention [4] includes the polycarbodiimide composition of any one of the above-described [1] to [3], wherein the alcohols contain an alcohol containing three or more consecutive oxyethylene groups, and 10 mass % or more and 40 mass % or less of the three or more consecutive oxyethylene groups are contained relative to the polycarbodiimide composition.

The present invention [5] includes the polycarbodiimide composition of any one of the above-described [1] to [4], wherein the alcohols contain an alcohol containing three or more consecutive oxyethylene groups, and 5 mol % or more and 50 mol % or less of the alcohol containing the three or more consecutive oxyethylene groups is contained relative to a total mol of the alcohols.

The present invention [6] includes the polycarbodiimide composition of any one of the above-described [1] to [5], wherein the polyisocyanate is aliphatic polyisocyanate.

The present invention [7] includes the polycarbodiimide composition of the above-described [6], wherein the aliphatic polyisocyanate is pentamethylene diisocyanate.

The present invention [8] includes a method for producing the polycarbodiimide composition of any one of the above-described [1] to [7], the method including the steps of: a urethane-formation step, in which the polyisocyanate and the alcohols are subjected to urethane-forming reaction, and a carbodiimide-formation step, in which the reaction product of the urethane-formation step is heated in the presence of a carbodiimide-formation catalyst to cause carbodiimide-formation reaction.

The present invention [9] includes the method for producing a polycarbodiimide composition of the above-described [8], wherein the reaction temperature in the carbodiimide-formation reaction is 125° C. or more and 160° C. or less.

The present invention [10] includes the method for producing a polycarbodiimide composition of the above-described [8] or [19], wherein the carbodiimide-formation reaction is performed while refluxing.

The present invention [11] includes an aqueous dispersion composition, wherein the aqueous dispersion composition is an aqueous dispersion in which the polycarbodiimide composition of any one of the above-described [1] to [7] is dispersed in water at a ratio of a solid content concentration of 5 mass % or more and 90 mass % or less.

The present invention [12] includes a solution composition, wherein the solution composition is a solution in which the polycarbodiimide composition of any one of the above-described [1] to [7] is dissolved in an organic solvent at a ratio of a solid content concentration of 5 mass % or more and 90 mass % or less.

The present invention [13] includes a resin composition containing a base component having a carboxyl group and a curing agent including the polycarbodiimide composition of any one of the above-described [1] to [7].

The present invention [14] includes a cured resin, wherein the cured resin is a cured product of the resin composition of the above-described [13].

Effects of the Invention

The polycarbodiimide composition of the present invention has the intensity ratio ($IR_{CI}/IR_{UI+U}$) of absorbance $IR_{CI}$ at or near 2120 cm$^{-1}$ due to stretching vibration of the carbodiimide group relative to the absorbance $IR_{UI+U}$ at or near 1720 cm$^{-1}$ due to stretching vibration of the uretonimine group and urethane group within a specific range.

Therefore, the polycarbodiimide composition of the present invention, the aqueous dispersion composition of the present invention and the solution composition of the present invention including the polycarbodiimide composition, and the resin composition of the present invention including the polycarbodiimide composition have excellent low temperature-fast curing properties.

Furthermore, with the method for producing a polycarbodiimide composition of the present invention, the polycarbodiimide composition of the present invention can be effectively produced.

The cured resin of the present invention is a cured product of the resin composition having excellent low temperature-fast curing properties. Therefore, the cured resin of the present invention is produced at a relatively low temperature and for a relatively short period of time, and has excellent various physical properties (e.g., water resistance, chemical resistance properties, etc).

DESCRIPTION OF EMBODIMENTS

Figure 1:
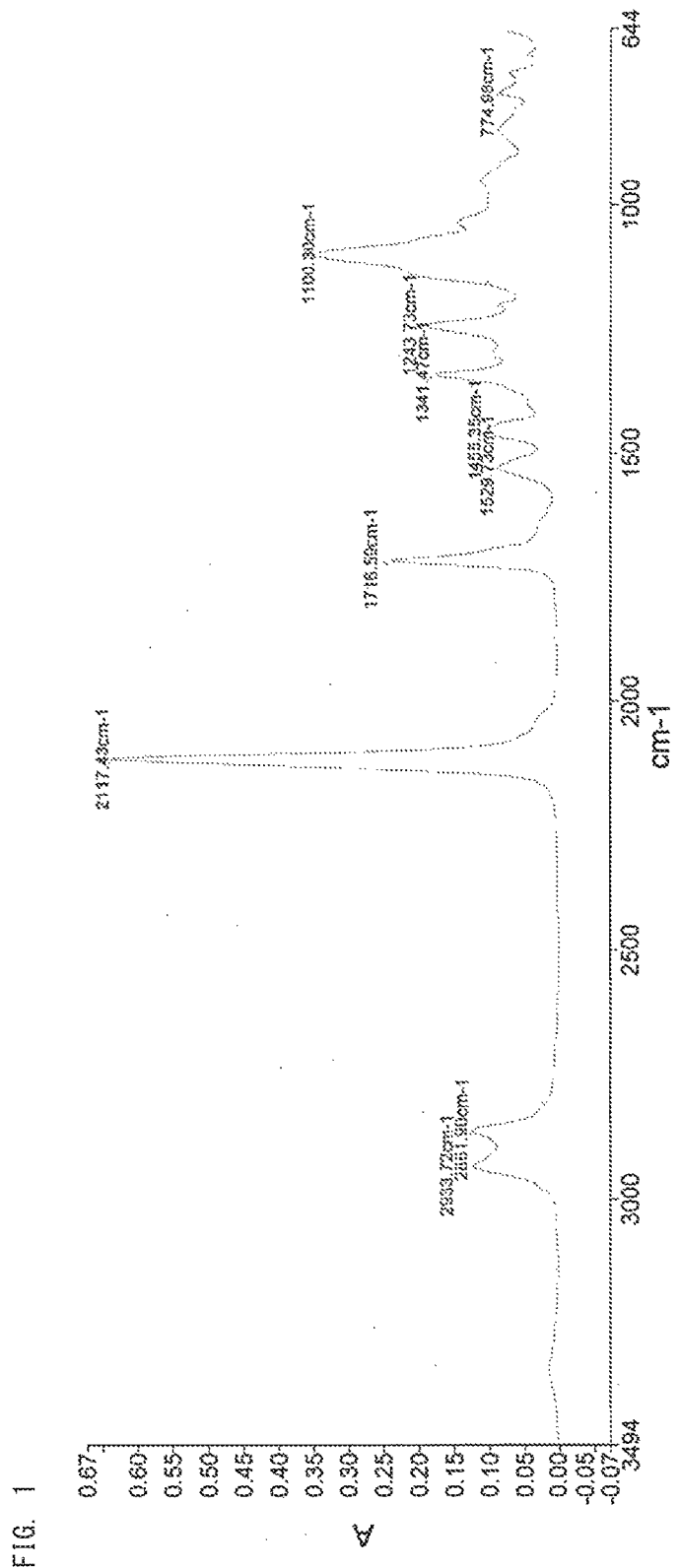
FIG. 1 shows an infrared absorption spectrum of the polycarbodiimide composition produced in Example 6.

A polycarbodiimide composition of the present invention is a reaction product of polyisocyanate having a primary isocyanate group (hereinafter, may be simply referred to as polyisocyanate) and alcohols.

The primary isocyanate group is defined as a monovalent functional group (—CH$_2$NCO) in which two hydrogen atoms (H) are bonded to the carbon atom (C) to which the isocyanate group (—NCO) is bonded.

For the polyisocyanate having a primary isocyanate group, those having at least one primary isocyanate group will suffice, and may include, for example, a secondary isocyanate group and a tertiary isocyanate group.

The secondary isocyanate group is defined as a difunctional group (—CHR—NCO (R represents a substituent)) in which one hydrogen atom (H) is bonded to the carbon atom (C) to which the isocyanate group (—NCO) is bonded.

The tertiary isocyanate group is defined as a trifunctional group (—CR$_1$R$_2$—NCO (R$_1$ and R$_2$ represent the same or different substituents)) in which no hydrogen atom (H) is bonded to the carbon atom (C) to which the isocyanate group (—NCO) is bonded.

For the polyisocyanate having a primary isocyanate group, for example, aliphatic polyisocyanate having a primary isocyanate group, alicyclic polyisocyanate having a primary isocyanate group, and araliphatic polyisocyanate having a primary isocyanate group are used.

The aliphatic polyisocyanate having a primary isocyanate group is an open-chain (straight chain or branched-chain: noncyclic) aliphatic polyisocyanate having a primary isocyanate group, and examples thereof include aliphatic diisocyanates such as ethylenediisocyanate, trimethylenediisocyanate, 1,2-propylenediisocyanate, butylenediisocyanate (tetramethylenediisocyanate, 1,2-butylenediisocyanate, 2,3-butylenediisocyanate, 1,3-butylenediisocyanate), 1,5-pentamethylene diisocyanate (PDI), 1,6-hexamethylenediisocyanate (HDI), 2,4,4- or 2,2,4-trimethylhexamethylenediisocyanate, 2,6-diisocyanatemethylcaproate, heptamethylenediisocyanate, octamethylenediisocyanate, and dodecamethylenediisocvanate.

Examples of the alicyclic polyisocyanate having a primary isocyanate group include alicyclic diisocyanates such as 3-isocyanatomethyl-3,5,5-trimethylcyclohexyl isocyanate (isophoron diisocyanate, IPDI), 1,3- or 1,4-bis(isocyanatomethyl)cyclohexane or a mixture thereof (hydrogenated XDI), and norbomanediisocyanate (NBDI).

Examples of the araliphatic polyisocyanate having a primary isocyanate group include araliphatic diisocyanates such as 1,3- or 1,4-xylylene diisocyanate or a mixture thereof (XDI).

These polyisocyanates having a primary isocyanate group may be used singly or in combination of two or more.

For the polyisocyanate having a primary isocyanate group, in view of light resistance, flowability, and water dispersiveness, preferably, the aliphatic polyisocyanate having a primary isocyanate group and alicyclic polyisocyanate having a primary isocyanate group are used, more preferably, the aliphatic polyisocyanate having a primary isocyanate group is used.

For the aliphatic polyisocyanate having a primary isocyanate group, in view of availability, preferably, 1,5-pentamethylene diisocyanate (PDI) and 1,6-hexamethylenediisocyanate (HDI) are used, more preferably, 1,5-pentamethylene diisocyanate (PDI) is used.

1,5-pentamethylene diisocyanate has less carbon atoms than that of 1,6-hexamethylenediisocyanate, and has a smaller molecular weight. Therefore, to produce a polycarbodiimide composition having the same molecular weight, use of 1,5-pentamethylene diisocyanate allows for a high carbodiimide group concentration in the polycarbodiimide composition compared with the case where 1,6-hexamethylenediisocyanate is used. As a result, a polycarbodiimide composition with excellent low temperature-fast curing properties can be produced, and furthermore, a cured resin (described later) with excellent physical properties (water resistance, chemical resistance properties, etc) can be produced. In addition, 1,5-pentamethylene diisocyanate having an odd number of carbon atoms has a low crystallinity due to amorphous structure based on the odd number carbon atoms compared with 1,6-hexamethylenediisocyanate having an even number of carbon atoms, and therefore has excellent flowability and dispersiveness, and improves physical properties of the produced cured resin (described later).

Furthermore, compared with the case where 1,6-hexamethylenediisocyanate is used, use of 1,5-pentamethylene diisocyanate allows thermal decomposition of the uretonimine group described later easily, and therefore the polycarbodiimide composition can be produced with excellent yield. Furthermore, it can be handled even under a low temperature, and therefore production of a high-molecular weight uretonimine can be suppressed.

When two or more types of polyisocyanates having a primary isocyanate group are used in combination, preferably, the aliphatic polyisocyanate having a primary isocyanate group is used in combination with the alicyclic polyisocyanate having a primary isocyanate group.

When the aliphatic polyisocyanate having a primary isocyanate group is used in combination with the alicyclic polyisocyanate having a primary isocyanate group, storage stability and pot life can be improved based on low reactivity of the alicyclic polyisocyanate, and fast curing properties can be improved due to high reactivity of the aliphatic polyisocyanate. That is, well-balanced storage stability and pot life, and fast curing properties can be achieved.

When the aliphatic polyisocyanate having a primary isocyanate group is used in combination with the alicyclic polyisocyanate having a primary isocyanate group, for example, 20 parts by mass or more, preferably 30 parts by mass or more, and for example, 90 parts by mass or less, preferably 50 parts by mass or less of the alicyclic polyisocyanate having a primary isocyanate group is used relative to 100 parts by mass of the aliphatic polyisocyanate having a primary isocyanate group.

When two or more types of polyisocyanates having a primary isocyanate group are used in combination, the timing of their mixing is not particularly limited, and they can be mixed in any of the steps described later (first urethane-formation step, carbodiimide-formation step, and second urethane-formation step).

To be specific, for example, two or more types of polyisocyanates can be used in combination in the first urethane-formation step (described later).

For example, after subjecting the two or more types of polyisocyanates individually to urethane-formation (first urethane-formation step (described later)), the two or more types of polyisocyanates that were subjected to urethane-formation can be mixed in the carbodiimide-formation step (described later).

For example, the two or more types of polyisocyanates can be subjected to urethane-formation (first urethane-formation step (described later)) and carbodiimide-formation (carbodiimide-formation step (described later)) individually, and then thereafter the two or more types of polyisocyanates that were subjected to the urethane-formation and carbodiimide-formation can be mixed in the second urethane-formation step (described later) and used.

Furthermore, for example, after subjecting one of the types of polyisocyanates to urethane-formation (first urethane-formation step (described later)), the polyisocyanate that was subjected to the urethane-formation can be mixed with the remaining type of polyisocyanate (polyisocyanate that was not subjected to urethane-formation) of the two or more types of polyisocyanates, and the mixture can be subjected to the carbodiimide-formation step (described later).

The above-described method can be used, without limitation, in addition to the case where two or more types of polyisocyanates are used in combination, also when polyisocyanate is used singly. For example, a portion of the single type of polyisocyanate is subjected to urethane-formation (first urethane-formation step (described later)), and thereafter, the polyisocyanate that went through urethane-formation can be mixed with the remaining portion of the single polyisocyanate (polyisocyanate that was not subjected to urethane-formation), and the mixture can be subjected to carbodiimide-formation step (described later).

Examples of the alcohols include alcohol containing three or more consecutive oxyethylene groups, and other alcohols (that is, alcohol containing no three or more consecutive oxyethylene groups).

For the alcohol containing three or more consecutive oxyethylene groups, for example, polyol containing three or more consecutive oxyethylene groups and monol containing three or more consecutive oxyethylene groups can be used.

The polyol containing three or more consecutive oxyethylene groups is an organic compound having three or more consecutive oxyethylene groups and two or more hydroxyl groups in combination in one molecule, and examples thereof include polyoxyethylene polyol.

Polyoxyethylene polyol can be produced by subjecting ethylene oxide to addition reaction so that the number of the repeating unit of the oxyethylene group is there or more using, for example, a low-molecular-weight polyol as an initiator.

The low-molecular-weight polyol is a compound having two or more hydroxyl groups and having a molecular weight of 60 or more and less than 500, and examples thereof include dihydric alcohols such as ethylene glycol, propylene glycol, 1,3-propanediol, 1,4-butyleneglycol, 1,3-butyleneglycol, 1,2-butyleneglycol, 1,5-pentanediol, 1,6-hexanediol, neopentyl glycol, 3-methyl-1,5-pentanediol, 2,2,2-trimethylpentanediol, 3,3-dimethylolheptane, alkane (C7 to 20)diol, 1,3- or 1,4-cyclohexanedimethanol and a mixture thereof, 1,3- or 1,4-cyclohexanediol and a mixture thereof, hydrogenated bisphenol A, 1,4-dihydroxy-2-butene, 2,6-dimethyl-1-octene-3,8-diol, bisphenol A, diethylene glycol, triethylene glycol, and dipropylene glycol; trihydric alcohols such as glycerin, trimethylolpropane, and triisopropanolamine; tetrahydric alcohols such as tetramethylolmethane (pentaerythritol), and diglycerin; pentahydric alcohols such as xylitol; hexahydric alcohols such as sorbitol, mannitol, allitol, iditol, dulcitol, altritol, inositol, and dipentaerythritol; heptahydric alcohols such as perseitol; and octahydric alcohols such as sucrose. These may be used singly or in combination of two or more.

For the low-molecular-weight polyol, preferably, dihydric alcohol is used.

Ethylene oxide can be subjected to addition reaction to these low-molecular-weight polyols by any method without particular limitation, and a known method can be used.

The functionality (hydroxyl group number) of the polyoxyethylene polyol is the same as the functionality (hydroxyl group number) of the initiator (low-molecular-weight polyol, etc), and for example, when dihydric alcohol is used for the initiator, polyoxyethylene glycol is produced as polyoxyethylene polyol.

These polyols containing three or more consecutive oxyethylene groups may be used singly or in combination of two or more.

For the polyol containing three or more consecutive oxyethylene groups, preferably, polyoxyethylene glycol is used.

The monol containing three or more consecutive oxyethylene groups is an organic compound having three or more consecutive oxyethylene groups and one hydroxyl group in combination in one molecule, and examples thereof include one-end terminated polyoxyethylene glycol.

The one-end terminated polyoxyethylene glycol is polyethylene glycol monoalkylether in which hydroxyl group at one end of polyoxyethylene glycol is replaced with an oxyalkylene group.

In polyethylene glycol monoalkylether, the number of carbon atoms in the alkyl group is 1 or more, for example, 20 or less, preferably 8 or less, and more preferably, 6 or less, even more preferably, 4 or less, particularly preferably; 2 or less. That is, examples of the alkyl group for terminating the one end include methyl group and ethyl group. For such polyethylene glycol monoalkylether, to be specific, polyethylene glycol monomethylether and polyethylene glycol monoethylether are used.

These monols containing three or more consecutive oxyethylene groups may be used singly or in combination of two or more.

These alcohols containing three or more consecutive oxyethylene groups may be used singly or in combination of two or more.

For the alcohol containing three or more consecutive oxyethylene groups, preferably, monol containing three or more consecutive oxyethylene groups, more preferably; polyethylene glycol monoalkylether, even more preferably; polyethylene glycol monomethylether is used.

In the alcohol containing three or more consecutive oxyethylene groups, the repeating unit of the oxyethylene group is 3 or more, preferably, 5 or more, more preferably, 10 or more, and for example, 60 or less, preferably 50 or less.

When the repeating unit of the oxyethylene group is within the above-described range, stability at the time of synthesis and water dispersiveness of the polycarbodiimide composition can be improved.

The alcohol containing three or more consecutive oxyethylene groups has a molecular weight (number average molecular weight) of, for example, 100 or more, preferably, 200 or more, more preferably, 300 or more, further preferably, 400) or more, and for example, 5000 or less, preferably 3000 or less, more preferably, 2000 or less, further preferably, 1000 or less.

When the alcohol containing three or more consecutive oxyethylene groups has a molecular weight (number average molecular weight) within the above-described range, stability at the time of synthesis and water dispersiveness of the polycarbodiimide composition can be improved.

Other alcohol is alcohol excluding the above-described alcohol containing three or more consecutive oxyethylene groups, and to be specific, alcohol having no three or more consecutive oxyethylene groups in its molecule. In other words, other alcohol is alcohol that contains no oxyethylene group, or contains no three or more consecutive oxyethylene groups (e.g., contains two consecutive oxyethylene group, single oxyethylene group, etc).

For the other alcohol, to be specific, polyol (hereinafter referred to as other polyol) excluding the above-described polyol containing three or more consecutive oxyethylene groups, and monol (hereinafter referred to as other monol) excluding the above-described monol containing three or more consecutive oxyethylene groups are used.

Other polyol is alcohol having no three or more consecutive oxyethylene groups in one molecule, and having two or more hydroxyl groups in one molecule. Examples thereof include aliphatic polyols having no oxyethylene group such as decanediol (number of carbons 10), dodecanediol (number of carbons 12), tetradecanediol (number of carbons 14), hexadecanediol (number of carbons 16), octadecanediol (number of carbons 18), and eicosane diol (number of carbons 20); and ether polyol having one to two oxyethylene groups such as diethylene glycol. These other polyols may be used singly or in combination of two or more.

Other monol is alcohol having no three or more consecutive oxyethylene groups in one molecule, and having one hydroxyl group in one molecule, and examples thereof include aliphatic monol having no oxyethylene group such as methanol, ethanol, propanol, isopropanol, butanol, hexanol, cyclohexanol, heptanol, octanol, 2-ethylhexanol, nonylalcohol, isononylalcohol, decanol (number of carbons 10), laurylalcohol (number of carbons 12), cetyl alcohol (number of carbons 16), stearyl alcohol (number of carbons 18), oleylalcohol (number of carbons 18), and eicosanol (number of carbons 20); ether monol having one to two oxyethylene groups such as 1-methoxy-2-propanol, 1-ethoxy-2-propanol, and diethylene glycol monoethylether (also called: carbitol); and aromatic alcohols such as phenol and a derivative thereof, benzylalcohol and a derivative thereof, phenethyl alcohol and a derivative thereof, and naphthol and a derivative thereof. These other monols may be used singly or in combination of two or more.

Other alcohols may be used singly or in combination of two or more.

For the other alcohol, preferably, other monol, more preferably, aliphatic monol having no oxyethylene group and ether monol having one to two oxyethylene groups are used, and in view of improvement in water dispersiveness, more preferably, ether monol having one to two oxyethylene groups, particularly preferably, I-methoxy-2-propanol is used.

These alcohols may be used singly or in combination of two or more.

In view of improvement in water dispersiveness, alcohols preferably contain three or more consecutive oxyethylene groups, and in view of achieving both water dispersiveness and water resistance, preferably, alcohol containing three or more consecutive oxyethylene groups and other alcohol are used in combination.

That is, when the alcohols contain the alcohol containing three or more consecutive oxyethylene groups, hydrophilicity can be improved, and therefore water dispersiveness of the polycarbodiimide composition can be improved, and the aqueous dispersion composition (described later) can be produced efficiently.

When the alcohols contain the alcohol containing three or more consecutive oxyethylene groups, the three or more consecutive oxyethylene groups is contained in an amount relative to the polycarbodiimide composition of, for example, 5 mass % or more, preferably, 10 mass % or more, more preferably 15 mass % or more, and for example, 50 mass % or less, preferably 40 mass % or less, more preferably, 35 mass % or less.

When the oxyethylene group content is within the above-described range, low temperature-fast curing properties and water dispersiveness of the polycarbodiimide composition can be improved, and a cured resin (described later) with excellent water resistance can be produced.

The above-described oxyethylene group content is the oxyethylene group content of the alcohol containing three or more consecutive oxyethylene groups, and does not include the oxyethylene group (e.g., oxyethylene group in the ether monol having one to two oxyethylene groups) content of the other polyol.

The three or more consecutive oxyethylene groups content can be calculated based on the formulation.

When the alcohols contain the alcohol containing three or more consecutive oxyethylene groups and other alcohol, the alcohol containing three or more consecutive oxyethylene groups is contained relative to a total mol of the alcohols in an amount of, for example, 5 mol % or more, preferably 12 mol % or more, and for example, 50 mol % or less, preferably 48 mol % or less. The other alcohol is contained in an amount of, for example, 50 mol % or more, preferably 52 mol % or more, and for example, 95 mol % or less, preferably 88 mol % or less.

When the alcohol containing three or more consecutive oxyethylene groups and other alcohol are contained in an amount within the above-described range, low temperature-fast curing properties and water dispersiveness of the polycarbodiimide composition can be improved, and a cured resin (described later) with excellent water resistance can be produced.

Meanwhile, the alcohols may only contain other alcohol without containing the alcohol containing three or more consecutive oxyethylene groups.

In this case, oleophilicity can be improved, and therefore solubility of the polycarbodiimide composition in the organic solvent can be improved, and the solution composition (described later) can be produced efficiently.

The polycarbodiimide composition can be produced by allowing the above-described polyisocyanate to react with the above-described alcohols under predetermined conditions, and furthermore, subjecting them to carbodiimide-formation reaction.

In the following, the method for producing the polycarbodiimide composition is further described.

In this method, first, the above-described polyisocyanate and the above-described alcohols are subjected to urethane-forming reaction (urethane-formation step).

In the urethane-formation step, the reaction ratio of the polyisocyanate to the alcohols is in a manner such that the equivalent ratio (NCO/OH) of the isocyanate group of polyisocyanate relative to the hydroxyl group in the alcohols is, for example, more than 2, preferably, 3 or more, more preferably, 4 or more, and for example, 16 or less, preferably 14 or less, more preferably, 10 or less. That is, in the urethane-formation step, preferably, reaction is caused in a manner such that the isocyanate group is excessive relative to the hydroxyl group.

When the reaction ratio of the polyisocyanate to the alcohols is within the above-described range, water dispersiveness and low temperature-fast curing properties of the polycarbodiimide composition can be improved.

In this reaction, as necessary, for example, a known urethane-formation catalyst such as amines and organic metal compounds can be added.

Examples of the amine include tertiary amines such as triethylamine, triethylenediamine, bis-(2-dimethylaminoethyl) ether, and N-methylmorpholine; quaternary ammonium salts such as tetraethyl hydroxyl ammonium; and imidazoles such as imidazole and 2-ethyl-4-methylimidazole.

Examples of the organic metal compound include organic tin compounds such as tin acetate, tin octylate, tin oleate, tin laurate, dibutyltin diacetate, dimethyltin dilaurate, dibutyltin dilaurate, dibutyltin dimercaptide, dibutyltin maleate, dibutyltin dilaurate (dibutyltin (IV) dilaurate), dibutyltin dineodecanoate, dioctyltin dimercaptide, dioctyltin dilaurate, and dibutyltin dichloride; organic lead compounds such as lead octanoate and lead naphthenate; organic nickel compounds such as nickel naphthenate; organic cobalt compounds such as cobalt naphthenate; organic copper compounds such as copper octenate; and organic bismuth compounds such as bismuth octylate and bismuth neodecanoate.

Examples of the urethane-formation catalyst also include potassium salts such as potassium carbonate, potassium acetate, and potassium octoate.

These urethane-formation catalysts may be used singly or in combination of two or more.

The urethane-formation catalyst can be blended in an amount that is not particularly limited, and the amount is set suitably in accordance with the purpose and application.

The reaction conditions in the urethane-formation step are, for example, under normal pressure and inactive gas (e.g., nitrogen gas) atmosphere, the reaction temperature is, for example, 30° C. or more, preferably 60° C. or more, and for example, 200° C. or less, preferably 180° C. or less. The reaction time is, for example, 1 hour or more, preferably 3 hours or more, and for example, 50 hours or less, preferably 40 hours or less.

The urethane-modified polyisocyanate (alcohol-modified product) can be produced in this manner. The urethane-modified polyisocyanate (alcohol-modified product) has an isocyanate group at its molecular terminal.

Next, in this method, the reaction solution including the above-described reaction product in the urethane-formation step is heated in the presence of a carbodiimide-formation catalyst, thereby subjecting the reaction solution including the above-described reaction product to carbodiimide-formation reaction (carbodiimide-formation step).

The carbodiimide-formation catalyst is not particularly limited, and examples thereof include a trialkyl phosphoric acid ester compound, phosphorene oxide compound, phosphorene sulfide compound, phosphine oxide compound, and phosphine compound.

For the trialkyl phosphoric acid ester, for example, trialkylphosphoric acid ester compounds having 3 to 24 carbon atoms such as trimethylphosphate, triethylphosphate, and trioctylphosphate are used.

Examples of the phosphorene oxide compound include phosphorene oxide compounds having 4 to 18 carbon atoms such as 3-methyl-1-phenyl-2-phosphorene-1-oxide (MPPO), 1-ethyl-3-methyl-2-phosphorene-1-oxide (EMPO), 1,3-dimethyl-2-phosphorene-1-oxide, 1-phenyl-2-phosphorene-1-oxide, 1-methyl-2-phosphorene-1-oxide, 1-ethyl-2-phosphorene-1-oxide, and double bond isomers thereof.

For the phosphorene sulfide compounds, phosphorene sulfide compounds having 4 to 18 carbon atoms such as 1-phenyl-2-phosphorene-1-sulfide are used.

For the phosphine oxide compounds, phosphine oxide compounds having 3 to 21 carbon atoms such as triphenylphosphine oxide and tritolylphosphine oxide are used.

For the phosphine compound, phosphine compounds having 3 to 30 carbon atoms such as bis(oxadiphenylphosphino) ethane are used.

These carbodiimide-formation catalysts may be used singly or in combination of two or more.

For the carbodiimide-formation catalyst, preferably, phosphorene oxide compounds are used, preferably, 3-methyl-1-phenyl-2-phosphorene-1-oxide and 1-ethyl-3-methyl-2-phosphorene-1-oxide are used.

Use of the above-described carbodiimide-formation catalyst allows for improvement in carbodiimide-formation activities, decrease in reaction temperature, and suppression of side reactions such as uretonimine-formation, which allows for production of the polycarbodiimide composition with a good yield, and improvement in carbodiimide group content.

In view of producing a cured resin (described later) with excellent water resistance as the carbodiimide-formation catalyst, particularly preferably, 3-methyl-1-phenyl-2-phosphorene-1-oxide is used.

The carbodiimide-formation catalyst is blended in an amount relative to 100 parts by mass of the polyisocyanate (polyisocyanate used in the urethane-formation step) of, for example, 0.01 parts by mass or more, preferably 0.05 parts by mass or more, and for example, 20 parts by mass or less, preferably 10 parts by mass or less.

The reaction conditions in the carbodiimide-formation step are set so that the produced polycarbodiimide composition has a carbodiimide group content in a specific range to be described later. To be more specific, in view of achieving progress in the carbodiimide-formation reaction, and reduction in uretonimine, the reaction conditions are as follows: under an atmosphere of normal pressure and inactive gas (nitrogen gas, etc), the reaction temperature is, for example, 125° C. or more, preferably 130° C. or more, more preferably, 135° C. or more, and for example, 160° C. or less, preferably 155° C. or less, more preferably, less than 155° C. The reaction time is, for example, 1 hour or more, preferably, 3 hours or more, and for example, 50 hours or less, preferably, 40 hours or less.

By causing reaction under such conditions, the reaction product (urethane-modified polyisocyanate) produced in the urethane-formation step undergoes decarboxylation condensation through the isocyanate group, which allows for efficient production of the carbodiimide group.

To be more specific, when the reaction temperature is the above-described lower limit or more, the produced uretonimine can accelerate the reaction of decomposition into the carbodiimide and isocyanate group, which allows for progress of carbodiimide-formation reaction. With the temperature less than the above-described lower limit, it is very difficult to cause such thermal decomposition reaction, the uretonimine content increases, and the carbodiimide group content decreases. The increase in uretonimine causes increase in the molecular weight, which may solidify the reaction solution. Meanwhile, when the reaction temperature is the above-described upper limit or less, polymerization loss can be decreased. When the temperature is more than the above-described upper limit, polymerization reaction other than the carbodiimide-formation and uretonimine-formation is accelerated, and not only the carbodiimide group content decreases, but increase in the molecular weight easily causes solidification of the reaction solution.

In the carbodiimide-formation step, in view of smoothly causing carbodiimide-formation reaction, and accelerating decarboxylation condensation, preferably, the reaction solution is refluxed in the presence of an organic solvent. That is, the carbodiimide-formation reaction is caused while refluxing.

Examples of the organic solvent include ketones such as acetone, methyl ethyl ketone, methylisobutylketone, and cyclohexanone; nitriles such as acetonitrile, alkylesters such as methyl acetate, ethyl acetate, butyl acetate, and isobutyl acetate; aliphatic hydrocarbons such as n-hexane, n-heptane, and octane; alicyclic hydrocarbons such as cyclohexane and methylcyclohexane; aromatic hydrocarbons such as toluene, xylene, and ethylbenzene; glycol ether esters such as methylcellosolveacetate, ethylcellosolveacetate, methylcarbitolacetate, ethylcarbitolacetate, ethylene glycol methylether acetate, ethylene glycol ethylether acetate, propylene glycol methylether acetate (PMA), 3-methyl-3-methoxybutylacetate, and ethyl-3-ethoxypropionate; ethers such as diethylether, tetrahydrofuran, dioxane, 1,2-dimethoxyethane, diethylene glycol dimethylether, diethylene glycol diethylether, dipropylene glycol dimethylether, dipropylene glycol diethylether, ethylene glycol diethylether, and 1,2-diethoxyethane; halogenated aliphatic hydrocarbons such as methyl chloride, methylene chloride, chloroform, carbon tetrachloride, methyl bromide, methylene iodide, and dichloroethane; aprotic polar solvents such as N-methylpyrrolidone, dimethylformamide, N,N'-dimethylacetamide, dimethyl sulfoxide, and hexamethylphosphonylamide. These organic solvents may be used singly or in combination of two or more.

For the organic solvent, preferably, an organic solvent with which the temperature at the time of refluxing is within the range of the above-described reaction temperature is used.

Examples of the organic solvent include, to be specific, xylene, ethylene glycol methylether acetate, and propylene glycol methylether acetate.

The organic solvent is blended in an amount that is not particularly limited, and the amount relative to 100 parts by mass of the polyisocyanate (polyisocyanate used in the urethane-formation step) is, for example, 50 parts by mass or more, preferably 100 parts by mass or more, and for example, 2000 parts by mass or less, preferably 500 parts by mass or less.

By refluxing the reaction solution in the presence of organic solvent, decomposition reaction of uretonimine is accelerated, while carbodiimide-formation reaction is caused smoothly, and carbon dioxide generated with the carbodiimide-formation of the isocyanate group can be eliminated, and therefore acceleration of carbodiimide-formation can be achieved.

With such a method, a polycarbodiimide composition containing the urethane group, carbodiimide group, and uretonimine group is produced.

To be more specific, first, a urethane group derived from the isocyanate group of polyisocyanate is produced in the urethane-formation step.

Then, when the reaction product (urethane-modified polyisocyanate) produced in the urethane-formation step is heated in the carbodiimide-formation step, the carbodiimide group derived from the isocyanate group at the molecule terminal is produced, and a portion of the produced carbodiimide group is allowed to react with the isocyanate group at the molecule terminal, thereby producing the uretonimine group.

Then, the portion of the uretonimine group undergoes thermal decomposition by continuous heating in the carbodiimide-formation step, and the carbodiimide group and the isocyanate group at the molecule terminal regenerate, and furthermore, the carbodiimide group derived from the isocyanate group at the molecule terminal is produced.

The isocyanate group of polyisocyanate is convened to the urethane group, carbodiimide group, and uretonimine group in this manner. As a result, a polycarbodiimide composition containing the urethane group, carbodiimide group, and uretonimine group is produced.

In the above-described method for producing a polycarbodiimide composition, the ratio of the conversion from the isocyanate group to the carbodiimide group relative to the conversion from the isocyanate group to the urethane group and uretonimine group is relatively larger.

To be more specific, in an infrared absorption spectrum of the polycarbodiimide composition, the intensity ratio of absorbance $IR_{CI}$ at or near 2120 $cm^{-1}$ due to stretching vibration of the carbodiimide group relative to absorbance $IR_{UT+U}$ at or near 1720 cm$^{-1}$ due to stretching vibration of the uretonimine group and urethane group ($IR_{CI}/IR_{UT+U}$) is 1.5 or more, preferably 1.8 or more, more preferably 2.4 or more, 4.5 or less, preferably 4.2 or less, more preferably 3.6 or less.

In the polycarbodiimide composition, when the above-described intensity ratio ($IR_{CI}/IR_{UT+U}$) is below the above-described lower limit, the amount of the carbodiimide group is relatively small, and therefore low temperature-fast curing properties are insufficient, and when the resin composition (described later) is cured at a relatively low temperature and for a relatively short period of time, various physical properties of the produced cured resin (described later), particularly chemical resistance properties are poor.

When the above-described intensity ratio ($IR_{CI}/IR_{UT+U}$) is more than the above-described upper limit, the amount of the carbodiimide group is relatively large, but the molecular weight is high, and dispersiveness to water and solubility to organic solvents are poor, and thus the aqueous dispersion composition (described later) and solution composition (described later) cannot be produced.

In this regard, when the above-described intensity ratio ($IR_{CI}/IR_{UT+U}$) is in the above-described specific range, the molecular weight is adjusted, and the aqueous dispersion composition (described later) and solution composition (described later) can be produced easily, and furthermore, the amount of the carbodiimide group can be made larger relatively to produce a resin composition (described later) having excellent low temperature-fast curing properties, and furthermore, by curing the resin composition, a cured resin (described later) having various excellent physical properties can be produced at a relatively low temperature and for a relatively short period of time.

The infrared absorption spectrum of the polycarbodiimide composition can be measured in conformity with Examples described later.

In the polycarbodiimide composition, the proportion of the uretonimine group relative to a total mol of the carbodiimide group and the uretonimine group is, for example, 1 mol % or more, preferably, more than 1 mol %, more preferably 1.5 mol % or more, more preferably 2 mol % or more, particularly preferably, 4 mol % or more, and for example, 20 mol % or less, preferably 15 mol % or less, more preferably 10 mol % or less, even more preferably 8 mol % or less.

When the proportion of the uretonimine group relative to a total mol of the carbodiimide group and the uretonimine group in the polycarbodiimide composition is within the above-described specific range, low temperature-fast curing properties can be improved, and a cured resin (described later) with various excellent physical properties can be produced. Furthermore, in the aqueous dispersion composition (described later), water dispersiveness can also be improved.

The proportion of the uretonimine group relative to a total mol of the carbodiimide group and the uretonimine group can be determined by $^{13}$C-NMR spectrum in conformity with Examples described later.

In this method, as necessary, the polycarbodiimide composition produced in the above-described carbodiimide-formation step can be further allowed to react with alcohols. In the following, the urethane-formation step before the carbodiimide-formation step may be referred to as a first urethane-formation step, and the urethane-formation step after the carbodiimide-formation step may be referred to as a second urethane-formation step.

To be specific, when the polycarbodiimide composition produced in the carbodiimide-formation step still has the isocyanate group at its molecular terminal, by allowing the polycarbodiimide composition to react with alcohols, the isocyanate group at the molecule terminal can be subjected to urethane-formation.

In the second urethane-formation step, for the alcohols, the above-described other alcohol (that is, alcohol containing no three or more consecutive oxyethylene groups) is used.

The amount of the alcohols blended in the second urethane-formation step is adjusted so that the total amount of the alcohols used in the first urethane-formation step and the alcohols used in the second urethane-formation step relative to the polyisocyanate used in the first urethane-formation step is at a specific ratio.

To be specific, the equivalent ratio (NCO/OH) of the isocyanate group of polyisocyanate relative to a total amount of hydroxyl group in the alcohols used in the first urethane-formation step and the hydroxyl group in the alcohols used in the second urethane-formation step is, for example, more than 2, preferably 3 or more, more preferably 4 or more, and for example, 16 or less, preferably 14 or less, more preferably 10 or less.

In this reaction, as necessary, the above-described urethane-formation catalyst can be added. The urethane-formation catalyst can be blended in an amount that is not particularly limited, and is set suitably in accordance with the purpose and application.

The reaction conditions in the second urethane-formation step are set so that the produced polycarbodiimide composition has a urethane group, carbodiimide group, and uretonimine group content within the above-described predetermined range. The reaction conditions in the second urethane-formation step are as follows: under normal pressure and inactive gas (e.g., nitrogen gas) atmosphere, and the reaction temperature is preferably in the same range as that of the reaction temperature in the above-described carbodiimide-formation step. The reaction time is, for example, 15 minutes or more, preferably, 30 minutes or more, and for example, 5 hours or less, preferably, 1 hour or less.

In this manner, the isocyanate group at the molecule terminal of the polycarbodiimide composition and the hydroxyl group of the alcohols undergo urethane-forming reaction.

As a result, a polycarbodiimide composition having no isocyanate group at its molecular terminal or having a reduced isocyanate group at its molecule terminal is produced.

The thus produced polycarbodiimide composition has the urethane group, carbodiimide group, and uretonimine group at the above-described predetermined ratio. That is, the above-described intensity ratio ($IR_{CI}/IR_{UT+U}$) is in the above-described specific range. Therefore, the molecular weight is adjusted, and the aqueous dispersion composition (described later) and the solution composition (described later) can be easily obtained, and furthermore, the amount of the carbodiimide group can be made relatively larger, and a resin composition (described later) having excellent low temperature-fast curing properties can be produced, and furthermore, by curing the resin composition, a cured resin (described later) having various excellent physical properties can be produced at a relatively low temperature and for a relatively short period of time.

When the second urethane-formation step is performed, alcohols derived by-products are increased, and the molecular weight rapidly increased, which reduces flowability and water dispersiveness, and low temperature-fast curing properties may be reduced. Therefore, preferably, only the first urethane-formation step and the carbodiimide-formation step are performed without performing the second urethane-formation step.

The method for producing a polycarbodiimide composition is not limited to the above-described method, and for example, the polyisocyanate, carbodiimide-formation catalyst, and alcohols can be blended all at once, and the mixture can be heated.

As necessary, from the polycarbodiimide composition, for example, the unreacted polyisocyanate, unreacted alcohols, low-molecular-weight compound (by-product), organic solvent, carbodiimide-formation catalyst, and urethane-formation catalyst can be removed by a known method such as distillation, extraction, and filtration.

To the polycarbodiimide composition, as necessary, known additives such as storage stabilizer (o-toluenesulfonamide, p-toluenesulfonamide, etc), plasticizer, anti-blocking agent, heat-resistant stabilizer, light stabilizer, antioxidant, releasing agent, catalyst, pigment, dye, lubricant, filler, and anti-hydrolysis agent can be further added at an arbitrary timing. The amount of additive blended is not particularly limited, and is set suitably in accordance with the purpose and application.

The polycarbodiimide composition may be used singly or in combination of two or more.

In the polycarbodiimide composition, the intensity ratio ($IR_{CI}/IR_{UI+U}$) of absorbance $IR_{CI}$ at or near 2120 $cm^{-1}$ due to stretching vibration of the carbodiimide group relative to absorbance $IR_{UI+U}$ at or near 1720 $cm^{-1}$ due to stretching vibration of the uretonimine group and urethane group is within a specific range. Therefore, such a polycarbodiimide composition has excellent low temperature-fast curing properties.

The above-described method for producing a polycarbodiimide composition allows for efficient production of the polycarbodiimide composition.

The polycarbodiimide composition has excellent low temperature-fast curing properties, and therefore can be suitably used as a curing agent for the resin composition.

The resin composition contains a curing agent including the polycarbodiimide composition, and a base component having a carboxyl group.

The curing agent is not particularly limited as long as it contains the polycarbodiimide composition, and prepared as, for example, an aqueous dispersion (hereinafter referred to as aqueous dispersion composition) in which the polycarbodiimide composition is dispersed in water, or a solution (hereinafter referred to as solution composition) in which the polycarbodiimide composition is dissolved in an organic solvent.

The aqueous dispersion composition contains the polycarbodiimide composition and water.

For the polycarbodiimide composition in the aqueous dispersion composition, preferably, a polycarbodiimide composition produced by subjecting a reaction product of alcohols including the alcohol containing three or more consecutive oxyethylene groups and polyisocyanate to carbodiimide-formation reaction is used.

That is, when the alcohol containing three or more consecutive oxyethylene groups is used in the production of the polycarbodiimide composition, the polycarbodiimide composition contains three or more consecutive oxyethylene groups. Such a polycarbodiimide composition is hydrophilic, and therefore easily dispersed in water.

The polycarbodiimide composition can be dispersed in water by a method without particular limitation. For example, water can be added to the polycarbodiimide composition, and the mixture can be stirred, or the polycarbodiimide composition can be added to water, and the mixture can be stirred. Preferably, water is added to the polycarbodiimide composition.

The ratio of the polycarbodiimide composition to water is not particularly limited, but the aqueous dispersion composition has a polycarbodiimide composition (resin component) concentration (that is, solid content concentration) of, for example, 5 mass % or more, preferably 10 mass % or more, and for example, 90 mass % or less, preferably, 80 mass % or less.

When the curing agent is an aqueous dispersion composition, compatibility with water-based resin (base component) can be improved, and a cured product with excellent water resistance and solvent resistance can be produced. Such a solution composition includes the above-described polycarbodiimide composition, and therefore has excellent low temperature-fast curing properties.

The solution composition contains a polycarbodiimide composition and an organic solvent.

For the polycarbodiimide composition in the solution composition, preferably, a polycarbodiimide composition produced by subjecting reaction product of other polyol and polyisocyanate to carbodiimide-formation reaction is used.

That is, when the alcohol containing three or more consecutive oxyethylene groups is not used in production of the polycarbodiimide composition, the polycarbodiimide composition does not contain three or more consecutive oxyethylene groups. Such a polycarbodiimide composition is hydrophobic, and therefore is dissolved easily in an organic solvent.

When the alcohol containing three or more consecutive oxyethylene groups is used in production of the polycarbodiimide composition, and the polycarbodiimide composition contains three or more consecutive oxyethylene groups, it can be dissolved in an organic solvent.

Examples of the organic solvent include the above-described organic solvents, and preferably, methyl ethyl ketone, methylisobutylketone, ethyl acetate, butyl acetate, toluene, and xylene are used.

The polycarbodiimide composition can be dissolved in an organic solvent by a method without particular limitation. For example, the organic solvent can be added to the polycarbodiimide composition, and the mixture can be stirred, or the polycarbodiimide composition can be added to the organic solvent, and the mixture can be stirred. Preferably, the organic solvent is added to the polycarbodiimide composition.

The ratio of the polycarbodiimide composition to the organic solvent is not particularly limited, and the solution composition has a polycarbodiimide composition (resin component) concentration (that is, solid content concentration) of, for example, 5 mass % or more, preferably, 10 mass % or more, and for example, 90 mass % or less, preferably, 80 mass % or less.

When the curing agent is a solution composition, compatibility to oil-based resin (base component) can be improved, and a cured product with excellent water resistance and solvent resistance can be produced. Such a solution composition contains the above-described polycarbodiimide composition, and therefore has excellent low temperature-fast curing properties.

Examples of the base component having a carboxyl group include water-based resin having a carboxyl group and oil-based resin having a carboxyl group.

Examples of the water-based resin having a carboxyl group include hydrophilic polymer having a carboxyl group, and to be specific, hydrophilic polyester resin having a carboxyl group, hydrophilic polyamide resin having a carboxyl group, hydrophilic polyurethane resin having a carboxyl group, hydrophilic acrylic resin having a carboxyl group, hydrophilic polyolefin (e.g., polypropylene, polyethylene, polypropylene-polyethylene (random-block) copolymer, and also polyolefin having four or more carbon atoms in the repeating unit) resin having a carboxyl group. These water-based resins having a carboxyl group may be used singly or in combination of two or more.

For the water-based resin having a carboxyl group, preferably, hydrophilic polyurethane resin having a carboxyl group and hydrophilic acrylic resin having a carboxyl group are used.

Examples of the oil-based resin having a carboxyl group include hydrophobic polymer having a carboxyl group, and to be specific, hydrophobic polyester resin having a carboxyl group, hydrophobic polyamide resin having a carboxyl group, hydrophobic polyurethane resin having a carboxyl group, hydrophobic acrylic resin having a carboxyl group, and hydrophobic polyolefin (e.g., polypropylene, polyethylene, polypropylene-polyethylene (random-block) copolymer, and also polyolefin having four or more carbon atoms in the repeating unit) resin having a carboxyl group. These oil-based resins having a carboxyl group may be used singly or in combination of two or more.

For the oil-based resin having a carboxyl group, preferably, hydrophobic polyurethane resin having a carboxyl group and hydrophobic acrylic resin having a carboxyl group are used.

These may be used singly or in combination of two or more.

For the base component and curing agent, preferably, a combination of the water-based resin for the base component, and the aqueous dispersion composition for the curing agent is used. Another preferable combination is the oil-based resin for the base component and the solution composition for the curing agent.

For the resin composition, in view of reducing the organic solvent and protecting earth environment, preferably, a combination of the water-based base component and aqueous dispersion composition is used.

The resin composition containing the above-described base component and the above-described curing agent will suffice without particular limitation. It can be a two-component type, with which the base component and the curing agent are separately prepared and mixed at the time of usage, or a one-component type, with which the base component and the curing agent are mixed in advance.

For the resin composition, preferably, a two-component type resin composition is used.

The base component content and the curing agent content relative to 100 parts by mass of their total is as follows. The base component content is, for example, 10 parts by mass or more, preferably, 30 parts by mass or more, and for example, 99.5 parts by mass or less, preferably, 95.0 parts by mass or less. The curing agent content is, for example, 0.5 parts by mass or more, preferably, 5 parts by mass or more, and for example, 90 parts by mass or less, preferably, 70 parts by mass or less.

The molar ratio of the carbodiimide group in the curing agent relative to the carboxyl group in the base component is, for example, 0.1 or more, preferably, 0.2 or more, and for example, 2.0 or less, preferably, 1.5 or less.

To the base component and the curing agent, as necessary, to one or both of them, additives such as epoxy resin, catalyst, coating improving agent, leveling agent, antifoaming agent, stabilizers such as an antioxidant and ultraviolet ray absorber, plasticizer, surfactant, pigment, filler, organic or inorganic fine particles, antifungal agent, and silane coupling agent can be added. The amount of the additive blended is determined in accordance with its purpose and use.

For the base component, the above-described water-based resin having a carboxyl group, and/or, the above-described oil-based resin having a carboxyl group, and other resin (e.g., hydroxy group-containing polyurethane resin, hydroxy group-containing acrylic resin, hydroxy group-containing polyester resin, melamine resin, etc) can be used in combination.

For the curing agent, the above-described polycarbodiimide composition, and other curing agent (e.g., polyisocyanate resin, epoxy resin, etc) can be used in combination.

In such a resin composition, the above-described polycarbodiimide composition is used as the curing agent, and therefore a cured resin with excellent low temperature quick-drying properties and various physical properties (water resistance and solvent resistance) can be produced.

The cured resin can be produced by a method without particular limitation. For example, when the resin composition is one component type, the resin composition is applied as is to an object to be coated or adherend. When the resin composition is a two-component type, the base component and the curing agent are mixed, and the produced mixture is applied to an object to be coated or adherend. Then, by heating and curing the resin composition, a cured resin is produced.

In the above-described resin composition, the curing temperature is relatively low temperature, to be specific, for example, 100° C. or less, preferably, 80° C. or less. For example, the curing temperature is 20° C. or more, preferably 30° C. or more.

The curing time is a relatively short period of time, to be specific, for example, 1 hour or less, preferably, 30 minutes or less. For example, the curing time is 1 minute or more, preferably 5 minutes or more.

As necessary, the cured resin obtained by heating and curing can be further dried.

In such a case, the drying temperature is at room temperature, and for example, 10° C. or more, preferably 15° C. or more, and for example, 40° C. or less, preferably 30° C. or less.

The drying time is, for example, 1 minute or more, preferably 5 minutes or more, and for example, 2 hours or less, preferably 1 hour or less.

The produced cured resin is a cured product of a resin composition having excellent low temperature-fast curing properties, and therefore can be produced at relatively low temperature for a relatively short period of time, and has excellent various physical properties (e.g., water resistance, chemical resistance properties, etc).

When the polycarbodiimide composition is produced by using aliphatic polyisocyanate, the cured resin produced by using the polycarbodiimide composition has excellent light resistance (weatherability) as well.

Therefore, the resin composition and cured resin is suitably used in various fields of, for example, a coating material, adhesive material (adhesive), pressure-sensitive adhesive material (pressure-sensitive adhesive), ink, sealant, molding material, foam and optical material, and also resin modifier that modifies resin such as polyester, polylactic acid, polyamide, and polyimide.

When it is used as a coating material, it can be used as, for example, a coating for plastic, coating for automobile exterior, coating for automobile interior, coating for electronic and electric material, coating for optical material (lens, etc), coating for building material, coating glass, coating for woodwork, film coating, coating for ink, coating for artificial and synthetic leather (coating agent), coating for (coating agent) cans, and coating for paper.

For the above-described plastic coating, for example, coating for molded articles in which plastic materials (e.g., various polymer materials such as polyolefins, ABS, polycarbonates, polyamides, polyesters and their composites) are used, to be specific, coating for housings (mobile phones, smartphone, personal computer, tablet, etc), coating for automobile components (automobile interior material and headlamp, etc), coating for household electric appliances, coating for robot material, coating for furniture, coating for stationary, coating for soft materials such as rubber, elastomer, and gel, coating for eyewear materials (lens, etc), and coating for optical lens of electronic devices (surface coat agent).

Examples of the above-described coating for automobile exterior include coating for new cars (intermediate, base, top coating, etc), coating for automobile repair (intermediate, base, top coating, etc), and coating for external components (aluminum wheel, bumper, etc).

When the above-described resin composition is used as a coating for automobile exterior, for the base component, the above-described water-based resin having a carboxyl group, and the above-described oil-based resin having a carboxyl group can be used. Preferably, water-based resin having a carboxyl group is used.

For the water-based resin having a carboxyl group, preferably, hydrophilic acrylic resin having a carboxyl group, hydrophilic polyurethane resin having a carboxyl group, hydrophilic polyester resin having a carboxyl group, more preferably hydrophilic acrylic resin having a carboxyl group, and hydrophilic polyester resin having a carboxyl group are used. The above-described water-based resin having a carboxyl group can be used in combination of two or more.

For the base component, the above-described water-based resin having a carboxyl group, and/or the above-described oil-based resin having a carboxyl group, and other resin (e.g., hydroxy group-containing polyurethane resin, hydroxy group-containing acrylic resin, hydroxy group-containing polyester resin, melamine resin, etc) can be used in combination.

When the above-described resin composition is used as a coating for automobile exterior, the base component has a solid content concentration of, generally, 5 mass % or more, preferably 20 mass % or more, more preferably 30 mass % or more, and for example, 80 mass % or less, preferably, 70 mass % or less, more preferably 60 mass % or less.

The base component has a solid content-based acid number of, for example, 5 mg KOH/g or more, preferably 10 mg KOH/g or more, and for example, 200 mg KOH/g or less, preferably 100 mg KOH/g or less.

For the curing agent, the above-described polycarbodiimide composition is used, and the polycarbodiimide composition and other curing agent (e.g., polyisocyanate resin, epoxy resin, etc) can be used in combination.

Examples of the above-described film coating include a coating for optical members (optical film, optical sheet, etc), coating material for optics, coating for fiber, coating for electronic and electric materials, coating for food package, coating for medical films, coating for cosmetics packages, coating for film decoration, and coating for release films.

Examples of the adhesive include adhesive for packaging materials, adhesive for electrical devices, adhesive for liquid crystal displays (LCD), adhesive for organic EL displays, adhesive for organic EL lighting, adhesive for display devices (electronic paper and plasma display, etc), adhesive for LEDs, adhesive for interior and exterior of automobiles, adhesive for electronic home appliances, adhesive for solar battery back sheets, and adhesive for various batteries (lithium ion battery, etc).

Examples of the above-described resin for ink includes vehicles for various inks (printing ink, screen ink, flexographic ink, gravure ink, jet ink, etc).

Use of the polycarbodiimide composition is not limited to the above-described use. For example, the polycarbodiimide composition can be suitably used for, as a solid, a hydrolysis inhibitor for polyester, polyamide resin, and polylactic acid. Alternatively, the polycarbodiimide composition can be suitably used for, as a liquid, a hydrolysis inhibitor for polyesterpolyol. The liquid polycarbodiimide composition can also be made into a composite with acid-modified polyolefin, for example, maleic acid modified polyolefin; made into a composite with polyolefin emulsion in which acid-modified polyolefin is dispersed in water, or as a curing agent thereof; made into a composite with acrylic emulsion containing acid site, or as a curing agent thereof; fixing agent for fiber such as carbon fiber and glass fiber; reinforcing agent for fiber-reinforced plastics such as CFRP and FRP, or sizing agent, or curing agent.

EXAMPLES

While in the following, the present invention is described with reference to Production Examples, Examples, and Comparative Examples, the present invention is not limited to any of them by no means. The "parts" and "%" are based on mass unless otherwise specified. The specific numerical values in blending ratio (content ratio), property value, and parameter used in the following description can be replaced with upper limit values (numerical values defined as "or less" or "below") or lower limit values (numerical values defined as "or more" or "above") of corresponding numerical values in blending ratio (content ratio), property value, and parameter described in the above-described "DESCRIPTION OF EMBODIMENTS".

Various measurement methods are described below:

<IR intensity ratio ($IR_{CI}/IR_{UI+U}$)>

From the polycarbodiimide composition, the organic solvent used in the reaction was distilled off. The desolvated polycarbodiimide composition (hereinafter referred to as "desolvated product") was subjected to measurement to obtain IR spectrum of the polycarbodiimide composition in accordance with the law of the art with the following apparatus and conditions.

Then, the intensity ratio ($IR_{CI}/IR_{UI+U}$) of the absorbance $IR_{CI}$ at or near 2120 $cm^{-1}$ due to stretching vibration of the carbodiimide group relative to the absorbance $IR_{UI+U}$ at or near 1720 $cm^{-1}$ due to C=O stretching vibration of the uretonimine group and urethane group was calculated.

IR measurement apparatus: manufactured by Perkin Elmer Inc. Frontier FT-IR

Measurement method: ATR (attenuated total reflection)

Wave number range: 4000 to 400 $cm^{-1}$

Resolving power 4 $cm^{-1}$

FIG. 1 shows the infrared absorption spectrum obtained in the above-described analysis for the polycarbodiimide composition of Example 6 described later.

<Proportion of the Uretonimine Group Relative to a Total Mol of the Carbodiimide Group and the Uretonimine Group>

$^{13}$C-NMR analysis was performed with the following devices and conditions using a desolvated product, the uretonimine group content relative to 1 mol of a total of the carbodiimide group and uretonimine group was calculated based on the following formula.
Tetramethylsilane (0 ppm) in $CDCL_3$ solvent was used as the basis of chemical shift (ppm).
Apparatus: ECA-500 (manufactured by JEOL Ltd.)
Conditions; measurement frequency: 125 MHz, solvent: $CDCL_3$, solute concentration: 50 mass %
Measurement temperature: room temperature, scanning times 8500
Repeating time: 3.0 seconds, pulse width: 30° (3.70μ seconds)
Assigned peak of carbon in carbodiimide group (N=C=N group in carbodiimide group): 139 ppm
Assigned peak of carbon in uretonimine group (C=O group in uretonimine group) (3H): 155 ppm
Mol % of uretonimine group/(uretonimine group+carbodiimide group)=(integration value of assigned peak of carbon in uretonimine group)/(integration value of assigned peak of carbon in uretonimine group+integration value of assigned peak of carbodiimide group)×100

Figure 2:
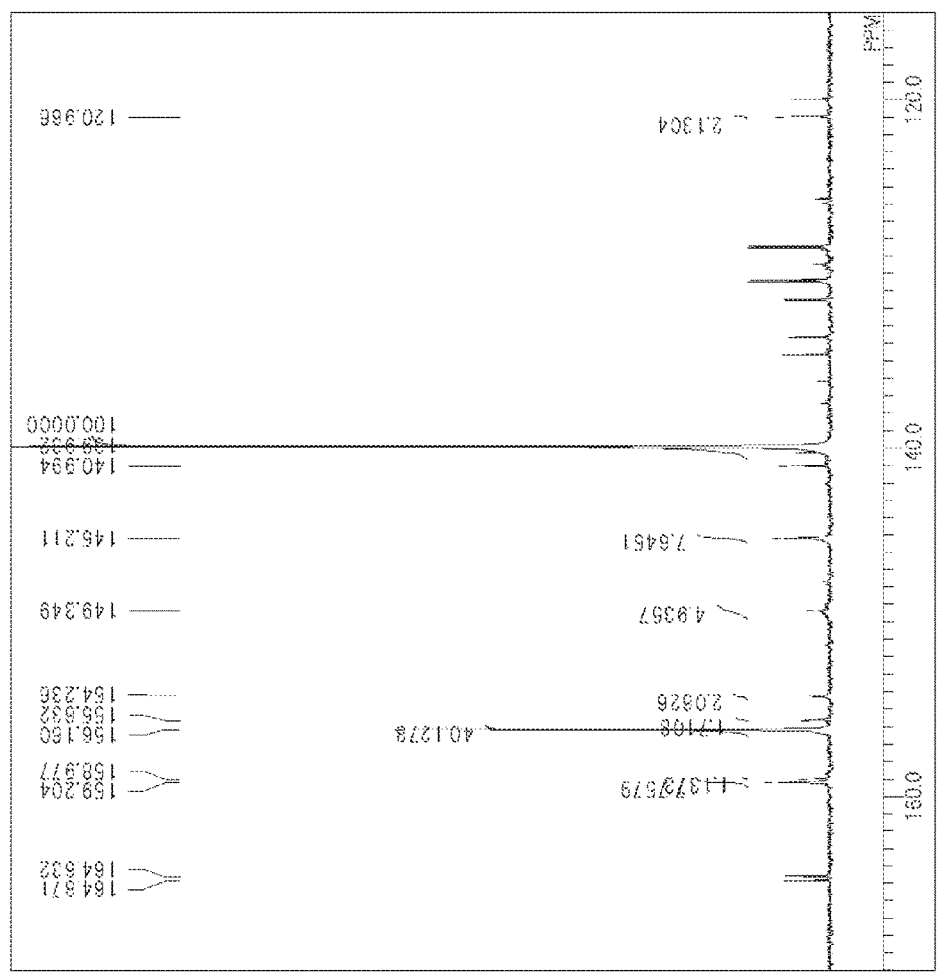
FIG. 2 shows a $^{13}$C-NMR spectrum of the polycarbodiimide composition produced in Example 20.

FIG. 2 shows $^{13}$C-NMR spectrum obtained in the above-described analysis on the polycarbodiimide composition of Example 20 described later.

<Amount of the Three or More Consecutive Oxyethylene Groups Contained in Polycarbodiimide Composition (Mass %)>

The oxyethylene group content relative to the polycarbodiimide composition was calculated from the amount charged and chemical structural formula.

<Amount of Alcohol Containing Three or More Consecutive Oxyethylene Groups Contained Relative to Total Mol of Alcohols (Mol %)>

Amount of alcohol containing three or more consecutive oxyethylene groups relative to a total mol of alcohols was calculated from the amount charged and chemical structural formula.

Production Example 1 (Production of Pentamethylene Diisocyanate)

99.9 mass % of 1,5-pentamethylene diisocyanate (hereinafter may be referred to as PDI) was produced in the same manner as in Example 1 of DESCRIPTION of WO2012/121291.

To be more specific, a pressurizing reactor with a jacket equipped with an electromagnetic induction stirrer, an automatic pressure control valve, a thermometer, a nitrogen inlet line, a phosgene inlet line, a condenser, and a material feed pump was charged with 2000 parts by mass of o-dichlorobenzene. Then, 2300 parts by mass of phosgene was added from the phosgene inlet line, and stirring was started. Cold water was allowed to go through the reactor jacket so that the internal temperature was kept to about 10° C. Then, a solution of 400 parts by mass of pentamethylenediamine (a) dissolved in 2600 parts by mass of o-dichlorobenzene was fed through the feed pump taking 60 minutes, and cold phosgenation was started at 30° C. or less and under normal pressure. After the completion of the feed, a light-brown white slurry was formed in the pressurized reactor.

Then, while the temperature of the internal liquid of the reactor was gradually increased to 160° C., the pressure was increased to 0.25 MPa, and further hot phosgenation was performed under a pressure of 0.25 MPa, and at a reaction temperature of 160° C. for 90 minutes. During the hot phosgenation, 1100 parts by mass of phosgene was further added. In the process of the hot phosgenation, the internal liquid of the pressurized reactor became light-brown clear solution. After completion of hot phosgenation, at 100 to 140° C., nitrogen gas was allowed to pass through at 100 L/hour, and degassing was performed.

Thereafter, o-dichlorobenzene was distilled off under reduced pressure, and then pentamethylene diisocyanate was distilled off also under reduced pressure, thereby producing 558 parts by mass of pentamethylene diisocyanate ($a_0$) with purity of 98.7%.

Then, a four-neck flask equipped with a stirrer, a thermometer, a reflux pipe, and a nitrogen inlet tube was charged with 558 parts by mass of pentamethylene diisocyanate ($a_0$), and 0.02 parts by mass of tris (tridecyl) phosphite (manufactured by Johoku Chemical Co., Ltd, trade name: JP-333E) relative to 100 parts by mass of pentamethylene diisocyanate, and while introducing nitrogen, heat treatment was performed under normal pressure, at 190° C., for 2 hours, thereby producing 553 parts by mass of pentamethylene diisocyanate ($a_1$) having a purity of 98.2%. The yield of pentamethylene diisocyanate in heat treatment was 99.4%.

Then, pentamethylene diisocyanate ($a_1$) after heat treatment was introduced to a glass-made flask, and using a distillation apparatus equipped with a distillation column (manufactured by SIBATA SCIENTIFIC TECHNOLOGY LTD., trade name: distillation column K type) having a distillation pipe charged with four elements of packing materials (manufactured by Sumitomo Heavy Industries, Ltd., trade name: Sumitomo/Sulzer Laboratory packing EX type) and a reflux ratio adjusting timer, and a condenser, the pentamethylene diisocyanate was rectified while further being refluxed under the conditions of 127 to 132° C. and 2.7 KPa, thereby taking fraction with a fraction rate of 20 to 80% and producing pentamethylene diisocyanate (a).

Example 1

Production of Polycarbodiimide Composition

A four-neck flask equipped with a stirrer, thermometer, reflux pipe, and nitrogen inlet tube was charged with 100.0 parts by mass of pentamethylene diisocyanate produced in Production Example 1, 40.0 parts by mass of UNIOXM550 (manufactured by NOF corporation, polyethylene glycol monomethylether, molecular weight 550), and 6.0 parts by mass of 1-methoxy-2-propanol under room temperature. Heating was conducted to 80° C. while introducing nitrogen under normal pressure, and stirring was conducted for 6 hours (first urethane-formation step).

Then, 306.5 parts by mass of xylene, and 2.0 parts by mass of 3-methyl-1-phenyl-2-phosphorene-1-oxide (MPPO) was introduced, and stirring was conducted for 8 hours while refluxing (141° C.)(carbodiimide-formation step).

With further refluxing, 6.8 parts by mass of 1-methoxy-2-propanol was introduced, and stirring was conducted for 30 minutes, and the reaction was terminated (second urethane-formation step).

After termination of reaction, cooling was conducted to 80° C., and xylene was distilled off under reduced pressure, thereby producing a polycarbodiimide composition. A portion of the produced polycarbodiimide composition was taken out, and subjected to measurement. As a result of the measurement on IR spectrum, the IR intensity ratio ($IR_{CI}/IR_{UI+U}$) was 2.83. $^{13}$C-NMR analysis was performed, and the proportion of the uretonimine group relative to a total mol of the carbodiimide group and the uretonimine group was 6.9 mol %.

Preparation of Aqueous Dispersion of Polycarbodiimide Composition (Aqueous Dispersion Composition)

The polycarbodiimide composition was put into a flask, heating was conducted to 80° C., and distilled water was gradually added so that the resin solid content was 40%. After stirring for 5 minutes, it was cooled to room temperature. In this manner, an aqueous dispersion of polycarbodiimide composition was produced. Thereafter, water dispersiveness was evaluated by the following methods.

Preparation of Resin Composition

The produced aqueous dispersion of polycarbodiimide composition was used as the curing agent. Then, 1.5 parts by mass of curing agent was mixed with 98.5 parts by mass of polyurethane dispersion (solid content 30 mass %, carboxyl group equivalent 3100 g/mol) as the base component, thereby preparing a resin composition.

Example 2

A four-neck flask equipped with a stirrer, thermometer, reflux pipe, and nitrogen inlet tube was charged with 100.0 parts by mass of pentamethylene diisocyanate produced in Production Example 1, 40.0 parts by mass of UNIOXM550, and 12.8 parts by mass of 1-methoxy-2-propanol under room temperature. Heating was conducted to 80° C. while introducing nitrogen under normal pressure, and stirring was conducted for 6 hours (urethane-formation step).

Then, 327.7 parts by mass of xylene, and 2.0 parts by mass of 3-methyl-1-phenyl-2-phosphorine-1-oxide were introduced, stirring was conducted for 8.5 hours while refluxing (141° C.), and the reaction was terminated (carbodiimide-formation step).

After termination of reaction, cooling was conducted to 80° C., and xylene was distilled off under reduced pressure, thereby producing a polycarbodiimide composition. The produced polycarbodiimide composition was taken out, and analyzed in the same manner as in Example 1. Tables 1 to 2 show the results.

Also, in the same manner as in Example 1, an aqueous dispersion of polycarbodiimide composition was prepared, thereby preparing a resin composition.

Example 3

A polycarbodiimide composition was produced in the same manner as in Example 2, except that 39.0 parts by mass of UNIOXM400 (manufactured by NOF corporation polyethylene glycol monomethylether, molecular weight 400) was used instead of UNIOXM550, and 10.7 parts by mass of 1-methoxy-2-propanol, and 314.1 parts by mass of xylene were used, and stirring was conducted for 8.5 hours while refluxing (141° C.).

The produced polycarbodiimide composition was taken out, and analyzed in the same manner as in Example 1. Tables 1 to 2 show the results.

Also, in the same manner as in Example 1, an aqueous dispersion of polycarbodiimide composition was prepared, thereby preparing a resin composition.

Example 4

A polycarbodiimide composition was produced in the same manner as in Example 2, except that 51.0 parts by mass of UNIOXM550, 30.6 parts by mass of 1-methoxy-2-propanol, and 380.2 parts by mass of xylene were used, and stirring was conducted for 8 hours while refluxing (141° C.).

The produced polycarbodiimide composition was taken out, and analyzed in the same manner as in Example 1. Tables 1 to 2 show the results.

Also, in the same manner as in Example 1, an aqueous dispersion of polycarbodiimide composition was prepared, thereby preparing a resin composition.

Example 5

A polycarbodiimide composition was produced in the same manner as in Example 2, except that 47.4 parts by mass of UNIOXM550, 21.5 parts by mass of 1-methoxy-2-propanol, and 353.9 parts by mass of xylene were used, and stirring was conducted for 8 hours while refluxing (141° C.).

The produced polycarbodiimide composition was taken out, and analyzed in the same manner as in Example 1. Tables 1 to 2 show the results.

Also, in the same manner as in Example 1, an aqueous dispersion of polycarbodiimide composition was prepared, thereby preparing a resin composition.

Example 6

A polycarbodiimide composition was produced in the same manner as in Example 2, except that 43.0 parts by mass of UNIOXM550, 9.7 parts by mass of 1-methoxy-2-propanol, and 320.2 parts by mass of xylene were used, and stirring was conducted for 8.5 hours while refluxing (141° C.).

The produced polycarbodiimide composition was taken out, and analyzed in the same manner as in Example 1. Tables 1 to 2 show the results.

Also, in the same manner as in Example 1, an aqueous dispersion of polycarbodiimide composition was prepared, thereby preparing a resin composition.

Example 7

A polycarbodiimide composition was produced in the same manner as in Example 2, except that 35.7 parts by mass of UNIOXM550, 5.8 parts by mass of 1-methoxy-2-propanol, and 297.2 parts by mass of xylene were used, and stirring was conducted for 9 hours while refluxing (141° C.).

The produced polycarbodiimide composition was taken out, and analyzed in the same manner as in Example 1. Tables 1 to 2 show the results.

Also, in the same manner as in Example 1, an aqueous dispersion of polycarbodiimide composition was prepared, thereby preparing a resin composition.

Example 8

A polycarbodiimide composition was produced in the same manner as in Example 2, except that 43.0 parts by mass of UNIOXM550, 10.7 parts by mass of cyclohexanol instead of 1-methoxy-2-propanol, and 322.5 parts by mass of xylene were used.

The produced polycarbodiimide composition was taken out, and analyzed in the same manner as in Example 1. Tables 1 to 2 show the results.

Also, in the same manner as in Example 1, an aqueous dispersion of polycarbodiimide composition was prepared, thereby preparing a resin composition.

Example 9

A polycarbodiimide composition was produced in the same manner as in Example 2, except that 11.7 parts by mass of UNIOXM550, 14.8 parts by mass of 1-methoxy-2-propanol, and 263.8 parts by mass of xylene were used, and stirring was conducted for 8.5 hours while refluxing (141° C.).

The produced polycarbodiimide composition was taken out, and analyzed in the same manner as in Example 1. Tables 1 to 2 show the results.

Also, in the same manner as in Example 1, an aqueous dispersion of polycarbodiimide composition was prepared, thereby preparing a resin composition.

Example 10

A polycarbodiimide composition was produced in the same manner as in Example 2, except that 89.2 parts by mass of UNIOXM1000 (manufactured by NOF corporation polyethylene glycol monomethylether, molecular weight 1000), 2.1 parts by mass of 1-methoxy-2-propanol, and 400.2 parts by mass of xylene were used, and stirring was conducted for 8.5 hours while refluxing (141° C.).

The produced polycarbodiimide composition was taken out, and analyzed in the same manner as in Example 1. Tables 1 to 2 show the results.

Also, in the same manner as in Example 1, an aqueous dispersion of polycarbodiimide composition was prepared, thereby preparing a resin composition.

Example 11

A polycarbodiimide composition was produced in the same manner as in Example 6, except that 320.2 parts by mass of butyl acetate was used instead of xylene, and stirring was conducted for 12 hours at 128° C.

The produced polycarbodiimide composition was taken out, and analyzed in the same manner as in Example 1. Tables 1 to 2 show the results.

Also, in the same manner as in Example 1, an aqueous dispersion of polycarbodiimide composition was prepared, thereby preparing a resin composition.

Example 12

A polycarbodiimide composition was produced in the same manner as in Example 6, except that 320.2 parts by mass of propylene glycol monomethylether acetate (PMA) was used instead of xylene, and stirring was conducted for 4 hours at 128° C.

The produced polycarbodiimide composition was taken out, and analyzed in the same manner as in Example 1. Tables 1 to 2 show the results.

Also, in the same manner as in Example 1, an aqueous dispersion of polycarbodiimide composition was prepared, thereby preparing a resin composition.

Example 13

A polycarbodiimide composition was produced in the same manner as in Example 6, except that 2.00 parts by mass of 1-ethyl-3-methyl-3-phosphorine-1-oxide (EMPO) was used instead of 3-methyl-1-phenyl-2-phosphorine-1-oxide (MPPO), and stirring was conducted for 5 hours while refluxing (141° C.).

The produced polycarbodiimide composition was taken out, and analyzed in the same manner as in Example 1. Tables 1 to 2 show the results.

Also, in the same manner as in Example 1, an aqueous dispersion of polycarbodiimide composition was prepared, thereby preparing a resin composition.

Example 14

A polycarbodiimide composition was produced in the same manner as in Example 2, except that 23.8 parts by mass of UNIOXM550, 3.9 parts by mass of 1-methoxy-2-propanol, and 518.7 parts by mass of propylene glycol monomethylether acetate (PMA) instead of xylene were used, and stirring was conducted for 10 hours while refluxing (150° C.).

The produced polycarbodiimide composition was taken out, and analyzed in the same manner as in Example 1. Tables 1 to 2 show the results.

Also, in the same manner as in Example 1, an aqueous dispersion of polycarbodiimide composition was prepared, thereby preparing a resin composition.

Example 15

A polycarbodiimide composition was produced in the same manner as in Example 2, except that 22.3 parts by mass of UNIOXM550, 3.7 parts by mass of 1-methoxy-2-propanol, and 511.8 parts by mass of ethylene glycol diethylether 1,2-diethoxyethane (trade name ethylglyme, manufactured by SANKYO CHEMICAL CO., LTD.) instead of xylene were used, and stirring was conducted for 16 hours while refluxing (125° C.).

The produced polycarbodiimide composition was taken out, and analyzed in the same manner as in Example 1. Tables 1 to 2 show the results.

Also, in the same manner as in Example 1, an aqueous dispersion of polycarbodiimide composition was prepared, thereby preparing a resin composition.

Example 16

A four-neck flask equipped with a stirrer, thermometer, reflux pipe, and nitrogen inlet tube was charged with 100.0 parts by mass of hexamethylenediisocyanate instead of pentamethylene diisocyanate, 39.4 parts by mass of UNIOXM550, and 8.9 parts by mass of 1-methoxy-2-propanol under room temperature. Heating was conducted to 80° C. while introducing nitrogen under normal pressure, and stirring was conducted for 6 hours (urethane-formation step).

Then, 311.1 parts by mass of xylene, and 2.0 parts by mass of 3-methyl-1-phenyl-2-phosphorine-1-oxide were introduced, stirring was conducted for 8 hours while refluxing (141° C.), and the reaction was terminated (carbodiimide-formation step).

After termination of reaction, cooling was conducted to 80° C., and xylene was distilled off under reduced pressure, thereby producing a polycarbodiimide composition. The produced polycarbodiimide composition was taken out, and analyzed in the same manner as in Example 1. Tables 1 to 2 show the results.

Also, in the same manner as in Example 1, an aqueous dispersion of polycarbodiimide composition was prepared, thereby preparing a resin composition.

Example 17

A four-neck flask equipped with a stirrer, thermometer, reflux pipe, and nitrogen inlet tube was charged with 100.0 parts by mass of 1,3-xylylene diisocyanate, 36.8 parts by mass of UNIOXM550, and 7.7 parts by mass of 1-methoxy-2-propanol under room temperature. Heating was conducted to 80° C. while introducing nitrogen under normal pressure, and stirring was conducted for 2 hours (urethane-formation step).

Then, 303.2 parts by mass of xylene, and 2.0 parts by mass of 3-methyl-1-phenyl-2-phosphorine-1-oxide were introduced, stirring was conducted for 3 hours while refluxing (141° C.), and the reaction was terminated (carbodiimide-formation step).

After termination of reaction, cooling was conducted to 80° C., and xylene was distilled off under reduced pressure, thereby producing a polycarbodiimide composition. The produced polycarbodiimide composition was taken out, and analyzed in the same manner as in Example 1. Tables 1 to 2 show the results.

Also, in the same manner as in Example 1, an aqueous dispersion of polycarbodiimide composition was prepared, thereby preparing a resin composition.

Example 18

A four-neck flask equipped with a stirrer, thermometer, reflux pipe, and nitrogen inlet tube was charged with 100.0 parts by mass of 1,3-bis(isocyanatomethyl)cyclohexane, and 35.6 parts by mass of UNIOXM550, and 7.4 parts by mass of 1-methoxy-2-propanol under room temperature. Heating was conducted to 80° C. while introducing nitrogen under normal pressure, and stirring was conducted for 7 hours (urethane-formation step).

Then, 300.3 parts by mass of propylene glycol methylether acetate (PMA) and 2.0 parts by mass of 3-methyl-1-phenyl-2-phosphorine-1-oxide were introduced, stirring was conducted for 10 hours while refluxing (150° C.), and the reaction was terminated (carbodiimide-formation step).

After termination of reaction, cooling was conducted to 80° C., propylene glycol methylether acetate (PMA) was distilled off under reduced pressure, thereby producing a polycarbodiimide composition. The produced polycarbodiimide composition was taken out, and analyzed in the same manner as in Example 1. Tables 1 to 2 show the results.

Also, in the same manner as in Example 1, an aqueous dispersion of polycarbodiimide composition was prepared, thereby preparing a resin composition.

Example 19

A four-neck flask equipped with a stirrer, thermometer, reflux pipe, and nitrogen inlet tube was charged with 100.0 parts by mass of isophoron diisocyanate, 31.1 parts by mass of UNIOXM550, and 6.5 parts by mass of 1-methoxy-2-propanol under room temperature. Heating was conducted to 80° C. while introducing nitrogen under normal pressure, and stirring was conducted for 10 hours (urethane-formation step).

Then, 289.1 parts by mass of propylene glycol methylether acetate (PMA), and 2.0 parts by mass of 3-methyl-1-phenyl-2-phosphorine-1-oxide were introduced, stirring was conducted for 12 hours while refluxing (150° C.), and the reaction was terminated (carbodiimide-formation step).

After termination of reaction, cooling was conducted to 80° C., propylene glycol methylether acetate (PMA) was distilled off under reduced pressure, thereby producing a polycarbodiimide composition. The produced polycarbodiimide composition was taken out, and analyzed in the same manner as in Example 1. Tables 1 to 2 show the results.

Also, in the same manner as in Example 1, an aqueous dispersion of polycarbodiimide composition was prepared, thereby preparing a resin composition.

Example 20

Production of Polycarbodiimide Composition

A four-neck flask equipped with a stirrer, thermometer, reflux pipe, and nitrogen inlet tube was charged with 100.0 parts by mass of pentamethylene diisocyanate and 16.7 parts by mass of 1-methoxy-2-propanol under room temperature. Heating was conducted to 80° C. while introducing nitrogen under normal pressure, and stirring was conducted for 6 hours (urethane-formation step).

Then, 245.8 parts by mass of xylene and 2.0 parts by mass of 3-methyl-1-phenyl-2-phosphorine-1-oxide were introduced, stirring was conducted for 8.5 hours while refluxing (141° C.), and the reaction was terminated (carbodiimide-formation step).

After termination of reaction, cooling was conducted to 80° C., and xylene was distilled off under reduced pressure, thereby producing a polycarbodiimide composition. Tables 1 to 2 show the results.

The produced polycarbodiimide composition was taken out, and analyzed in the same manner as in Example 1. The IR intensity ratio ($IR_{CI}/IR_{UT+U}$) was 2.3. $^{13}C$-NMR analysis was performed, and the proportion of the uretonimine group relative to a total mol of the carbodiimide group and the uretonimine group was 7.1 mol %.

Preparation of Polycarbodiimide Composition Solution (Solution Composition)

The polycarbodiimide composition was put into a flask, heating was conducted to 80° C., and butyl acetate was gradually added so that the resin solid content was 40%. After stirring for 5 minutes, cooling to room temperature was conducted. A polycarbodiimide composition solution was produced in this manner.

Preparation of Resin Composition

The produced polycarbodiimide composition solution was used as the curing agent. Then, 1.0 part by mass of curing agent, 39.2 parts by mass of acrylic resin (solid content 50 mass %, solid content carboxyl group equivalent 2004 g/mol) as the base component, and 59.8 parts by mass of butyl acetate as the solvent were mixed, thereby preparing a resin composition.

Example 21

A four-neck flask equipped with a stirrer, thermometer, reflux pipe, and nitrogen inlet tube was charged with 42.0 parts by mass of 1,3-bis(isocyanatomethyl)cyclohexane, 52.9 parts by mass of UNIOXM550, and 10.8 parts by mass of 1-methoxy-2-propanol. Heating was conducted to 80° C. while introducing nitrogen under normal pressure, and stirring was conducted for 7 hours (urethane-formation step).

Then, 100 parts by mass of pentamethylene diisocyanate, 431.8 parts by mass of PMA, and 2.8 parts by mass of 3-methyl-1-phenyl-2-phosphorine-1-oxide were introduced, stirring was conducted for 9 hours while refluxing (150° C.), and the reaction was terminated (carbodiimide-formation step).

After termination of reaction, cooling was conducted to 80° C., and xylene was distilled off under reduced pressure, thereby producing a polycarbodiimide composition. The produced polycarbodiimide composition was taken out, and analyzed in the same manner as in Example 1. The results are shown in Table 3.

Also, in the same manner as in Example 1, an aqueous dispersion of polycarbodiimide composition was prepared, thereby preparing a resin composition.

Example 22

A four-neck flask equipped with a stirrer, thermometer, reflux pipe, and nitrogen inlet tube was charged with 100 parts by mass of pentamethylene diisocyanate and 10.8 parts by mass of 1-methoxy-2-propanol. Heating was conducted to 80° C. while introducing nitrogen under normal pressure, and stirring was conducted for 6 hours. A four-neck flask equipped with a stirrer, thermometer, reflux pipe, and nitrogen inlet tube was charged with 42.0 parts by mass of 1,3-bis(isocyanatomethyl)cyclohexane and 52.9 parts by mass of UNIOXM550. Heating was conducted to 80° C. while introducing nitrogen under normal pressure, and stirring was conducted for 7 hours (urethane-formation step).

Then, a four-neck flask equipped with a stirrer, thermometer, reflux pipe, and nitrogen inlet tube was charged with 110.8 parts by mass of pentamethylene diisocyanate subjected to urethane-formation, 94.9 parts by mass of 1,3-bis(isocyanatomethyl)cyclohexane subjected to urethane-formation, 431.8 parts by mass of PMA, and 2.8 parts by mass of 3-methyl-1-phenyl-2-phosphorine-1-oxide, stirring was conducted for 9 hours while refluxing (150° C.), and the reaction was terminated (carbodiimide-formation step).

After termination of reaction, cooling was conducted to 80° C., and xylene was distilled off under reduced pressure, thereby producing a polycarbodiimide composition. The produced polycarbodiimide composition was taken out, and analyzed in the same manner as in Example 1. The results are shown in Table 3.

Also, in the same manner as in Example 1, an aqueous dispersion of polycarbodiimide composition was prepared, thereby preparing a resin composition.

Comparative Example 1

A polycarbodiimide composition was produced in the same manner as in Example 2, except that 118.9 parts by mass of UNIOXM550, 39.0 parts by mass of 1-methoxy-2-propanol, and 538.2 parts by mass of xylene were used, and stirring was conducted for 7 hours while refluxing (141° C.).

The produced polycarbodiimide composition was taken out, and analyzed in the same manner as in Example 1. The results are shown in Table 4.

Also, in the same manner as in Example 1, an aqueous dispersion of polycarbodiimide composition was prepared, thereby preparing a resin composition.

Comparative Example 2

A polycarbodiimide composition was produced in the same manner as in Example 2, except that 17.8 parts by mass of UNIOXM550, 2.92 parts by mass of 1-methoxy-2-propanol, and 491.1 parts by mass PMA instead of xylene were used, and stirring was conducted for 11 hours while refluxing (150° C.).

The produced polycarbodiimide composition was taken out, and analyzed in the same manner as in Example 1. The results are shown in Table 4.

Thereafter, preparation of an aqueous dispersion of polycarbodiimide composition was conducted in the same manner as in Example 1, but the polycarbodiimide composition sedimented, and an aqueous dispersion could not be obtained.

Comparative Example 3

Example 6 was repeated except that 320.2 parts by mass of toluene instead of xylene was used and stirring was conducted at 115° C., but when 20 hours elapsed at 115° C., the reaction solution was solidified.

The produced polycarbodiimide composition was analyzed. The results are shown in Table 4.

Thereafter, preparation of an aqueous dispersion of polycarbodiimide composition was conducted in the same manner as in Example 1, but the polycarbodiimide composition sedimented, and an aqueous dispersion could not be obtained.

Comparative Example 4

Example 6 was repeated except that 320.2 parts by mass of tetralin instead of xylene was used, and stirring was conducted at 195° C., but when 4 hours elapsed at 195° C. the reaction solution solidified.

The produced polycarbodiimide composition was analyzed. The results are shown in Table 4.

Thereafter, preparation of aqueous dispersion of polycarbodiimide composition was conducted in the same manner as in Example 1, but the polycarbodiimide composition sedimented, and an aqueous dispersion could not be obtained.

Comparative Example 5

A polycarbodiimide composition was synthesized referring to the method described in Synthesis Example 83 of Patent publication No. 3630527.

To be specific, a four-neck flask equipped with a stirrer, thermometer, reflux pipe, and nitrogen inlet tube was charged with 1008 parts by mass of hexamethylenediisocyanate, and 800 parts by mass of UNIOXM400 (manufactured by NOF corporation polyethylene glycol monomethylether, molecular weight 400) under room temperature. Heating was conducted to 120° C. while introducing nitrogen under normal pressure, and stirring was conducted for 1 hour. Then, 13.5 parts by mass of 3-methyl-1-phenyl-2-phosphorene-1-oxide was introduced, and an attempt was made to conduct heating to 185° C. under nitrogen flow and stirring for 5 hours, but when 2 hours elapsed, the reaction solution solidified.

The produced polycarbodiimide composition was analyzed. The results are shown in Table 4.

Thereafter, preparation of aqueous dispersion of polycarbodiimide composition was conducted in the same manner as in Example 1, but the polycarbodiimide composition sedimented, and an aqueous dispersion could not be obtained.

Comparative Example 6

A polycarbodiimide composition was synthesized referring to the method described in Example 8 of U.S. Pat. No. 2,853,473A.

To be specific, a four-neck flask equipped with a stirrer, thermometer, reflux pipe, and nitrogen inlet tube was charged with 100.0 parts by mass of hexamethylenediisocyanate, 39.4 parts by mass of UNIOXM550, and 8.9 parts by mass of 1-methoxy-2-propanol under room temperature. Heating was conducted to 80° C. while introducing nitrogen under normal pressure, and stirring was conducted for 6 hours. Then, 2 parts by mass of 1-ethyl-3-methyl-3-phosphorene-1-oxide was introduced to the solution, heating was conducted under normal pressure to 80° C., and stirring was conducted for 2 hours. Furthermore, an attempt was made to conduct heating to 120° C. under nitrogen flow and stirring for 16 hours, but the reaction solution solidified after elapse of 14 hours.

The produced polycarbodiimide composition was analyzed. The results are shown in Table 4.

Thereafter, preparation of aqueous dispersion of polycarbodiimide composition was conducted in the same manner as in Example 1, but the polycarbodiimide composition sedimented, and an aqueous dispersion could not be obtained.

<Evaluation>

Flowability Evaluation

The organic solvent used in the reaction was distilled off from the polycarbodiimide composition, and flowability of the polycarbodiimide composition was visually evaluated. Evaluation criteria are shown below.
3 good flowability was kept.
2 low in flowability but no solidification.
1 solidified and lost flowability completely.

Water Dispersiveness Evaluation

In preparation of the aqueous dispersion of polycarbodiimide composition (excluding Example 20), water dispersiveness of the polycarbodiimide composition was visually evaluated. Evaluation criteria are shown below.
4 good dispersion with no presence of inhomogeneity.
3 slight presence of inhomogeneity but dispersion occurred.
2 presence of inhomogeneity but partially dispersed.
1 no dispersion at all and sedimented.

With those Examples and Comparative Examples evaluated as having water dispersiveness of 1, it was difficult to evaluate the coating precisely (described later), and therefore the coating was not evaluated.

Coating Evaluation

The resin composition was applied to a standard test plate (JIS-G-3303 SPTE) using a 250 mil doctor blade. Thereafter, the resin composition was dried at 80° C. for 10 minutes and 30 minutes, and dried further at room temperature for 1 hour, thereby producing a coating made of the cured resin. The produced coating was evaluated by the following method.

<Coating Properties>

Appearance of coating (80° C., 10 minutes) was visually evaluated. Evaluation criteria are shown below.
4 clear and smooth coating.
3 slightly inhomogeneous.
2 inhomogeneous.
1 very inhomogeneous.

<Water Resistance>

Spots of distilled water was placed on the coating (80° C., 10 minutes), and changes in appearances of the coating was visually checked after the coating was allowed to stand at 23° C. for 24 hours. Evaluation criteria are shown below.
4 no changes.
3 some whitening occurred.
2 slight whitening occurred.
1 whitening occurred.

<Solvent Resistance (Chemical Resistance Properties)>

The coating (80° C., 10 minutes and 30 minutes) was rubbed with a gauze soaked in methyl ethyl ketone (in Example 20, 50% aqueous solution of ethanol) while applying a load of 50 g, and the time until the coating broke was measured. Evaluation criteria are shown below.
4 coating was broken after 300 times or more of rubbing
3 coating was broken after rubbing of 250 times or more to less than 300 times of rubbing.
2 coating was broken after 100 times or more to less than 250 times of rubbing.
1 coating was broken after less than 100 times of rubbing.

TABLE 1

| No. | | | | Example 1 | Example 2 | Example 3 | Example 4 | Example 5 | Example 6 | Example 7 | Example 8 | Example 9 | Example 10 |
|---|---|---|---|---|---|---|---|---|---|---|---|---|---|
| (First) Urethane-formation step | Mixing formulation | Polyisocyanate | Type | PDI | PDI | PDI | PDI | PDI | PDI | PDI | PDI | PDI | PDI |
| | | | Parts by mass | 100 | 100 | 100 | 100 | 100 | 100 | 100 | 100 | 100 | 100 |
| | | Alcohol containing three or more consecutive oxyethylene groups | Type | Uniox M550 | Uniox M550 | Uniox M400 | Uniox M550 | Uniox M550 | Uniox M550 | Uniox M550 | Uniox M550 | Uniox M550 | Uniox M1000 |
| | | | Parts by mass | 40.0 | 40.0 | 39.0 | 51.0 | 47.4 | 43.0 | 35.7 | 43.0 | 11.7 | 89.2 |
| | | Other alcohol | Type | 1-methoxy-2-propanol | 1-methoxy-2-propanol | 1-methoxy-2-propanol | 1-methoxy-2-propanol | 1-methoxy-2-propanol | 1-methoxy-2-propanol | 1-methoxy-2-propanol | Cyclo-hexanol | 1-methoxy-2-propanol | 1-methoxy-2-propanol |
| | | | Parts by mass | 6.0 | 12.8 | 10.7 | 30.6 | 21.5 | 9.7 | 5.8 | 10.7 | 14.8 | 2.1 |
| | Reaction conditions | Reaction temperature | °C. | 80 | 80 | 80 | 80 | 80 | 80 | 80 | 80 | 80 | 80 |
| | | Reaction time | Hours | 6 | 6 | 6 | 6 | 6 | 6 | 6 | 6 | 6 | 6 |
| Carbodiimide-formation step | Mixing formulation | Organic solvent | Type | Xylene | Xylene | Xylene | Xylene | Xylene | Xylene | Xylene | Xylene | Xylene | Xylene |
| | | | Parts by mass | 306.5 | 327.7 | 314.1 | 380.2 | 353.9 | 320.2 | 297.2 | 322.5 | 263.8 | 400.2 |
| | | Catalyst | Type | MPPO | MPPO | MPPO | MPPO | MPPO | MPPO | MPPO | MPPO | MPPO | MPPO |
| | | | Parts by mass | 2.0 | 2.0 | 2.0 | 2.0 | 2.0 | 2.0 | 2.0 | 2.0 | 2.0 | 2.0 |
| | Reaction conditions | Reaction temperature | °C. | 141 | 141 | 141 | 141 | 141 | 141 | 141 | 141 | 141 | 141 |
| | | Reaction time | Hours | 8 | 8.5 | 8.5 | 8 | 8 | 8.5 | 9 | 8.5 | 8.5 | 8.5 |
| (Second) Urethane-formation step | Mixing formulation | Other alcohol | Type | 1-methoxy-2-propanol | None | None | None | None | None | None | None | None | None |
| | | | Parts by mass | 6.8 | | | | | | | | | |
| | Reaction conditions | Reaction temperature | °C. | 141 | | | | | | | | | |
| | | Reaction time | Hours | 0.5 | | | | | | | | | |
| Analysis | Equivalent ratio $R_{Total}$(NCO/OH) | | | 6.0 | 6.0 | 6.0 | 3.0 | 4.0 | 7.0 | 10.0 | 7.0 | 7.0 | 7.0 |
| | Alcohol containing three or more consecutive oxyethylene groups/Total alcohol amount(mol %) | | | 34 | 34 | 45 | 21 | 27 | 42 | 50 | 42 | 11 | 87 |
| | Three or more consecutive oxyethylene groups/Polycarbodiimide composition(mass %) | | | 25.5 | 25.5 | 25.1 | 27.3 | 27.3 | 27.4 | 24.5 | 27.2 | 9.0 | 45.4 |
| | Carbodiimide/ (Uretonimine + Urethane) | IR intensity ratio | | 2.8 | 2.6 | 2.6 | 1.6 | 1.9 | 2.7 | 3.2 | 2.5 | 2.7 | 2.7 |
| | Uretonimine/ (Carbodiimide + Uretonimine) | mol % | | 6.9 | 6.7 | 6.6 | 7.7 | 7.1 | 6.6 | 5.9 | 6.1 | 6.9 | 6.2 |
| Evaluation | Flowability | | | 2 | 3 | 3 | 3 | 3 | 3 | 3 | 3 | 3 | 3 |
| | Water dispersiveness (80° C., 40%) | | | 3 | 4 | 4 | 4 | 4 | 4 | 4 | 4 | 2 | 4 |
| | Coating 80° C. | Coating properties | | 2 | 3 | 4 | 3 | 3 | 3 | 3 | 3 | 1 | 3 |
| | | Water resistant characteristics | | 4 | 4 | 4 | 3 | 4 | 4 | 4 | 4 | 4 | 4 |
| | | Chemical resistance (10 minutes) | | 4 | 4 | 4 | 3 | 4 | 4 | 4 | 4 | 4 | 4 |
| | | Chemical resistance (30 minutes) | | 4 | 4 | 4 | 3 | 4 | 4 | 4 | 4 | 4 | 4 |

TABLE 2

| No. | | | | Example 11 | Example 12 | Example 13 | Example 14 | Example 15 | Example 16 | Example 17 | Example 18 | Example 19 | Example 20 |
|---|---|---|---|---|---|---|---|---|---|---|---|---|---|
| (First) Urethane-formation step | Mixing formulation | Polyisocyanate | Type | PDI | PDI | PDI | PDI | PDI | PDI | PDI | PDI | PDI | PDI |
| | | | Parts by mass | 100 | 100 | 100 | 100 | 100 | 100 | 100 | 100 | 100 | 100 |
| | | Alcohol containing three or more consecutive oxyethylene groups | Type | Uniox M550 | Uniox M550 | Uniox M400 | Uniox M550 | Uniox M550 | Uniox M550 | Uniox M550 | Uniox M550 | Uniox M550 | — |
| | | | Parts by mass | 40.0 | 40.0 | 39.0 | 51.0 | 47.4 | 43.0 | 35.7 | 43.0 | 11.7 | — |
| | | Other alcohol | Type | 1-methoxy-2-propanol | 1-methoxy-2-propanol | 1-methoxy-2-propanol | 1-methoxy-2-propanol | 1-methoxy-2-propanol | 1-methoxy-2-propanol | 1-methoxy-2-propanol | Cyclo-hexanol | 1-methoxy-2-propanol | 1-methoxy-2-propanol |
| | | | Parts by mass | 9.7 | 9.7 | 9.7 | 3.9 | 3.7 | 8.9 | 7.7 | 7.4 | 6.5 | 16.7 |
| | Reaction conditions | Reaction temperature | °C. | 80 | 80 | 80 | 80 | 80 | 80 | 80 | 80 | 80 | 80 |
| | | Reaction time | Hours | 6 | 6 | 6 | 6 | 6 | 6 | 2 | 7 | 10 | 6 |
| Carbodiimide-formation step | Mixing formulation | Organic solvent | Type | Butyl acetate | PMA | Xylene | PMA | Ethylglyme | Xylene | Xylene | PMA | PMA | Xylene |
| | | | Parts by mass | 320.2 | 320.2 | 320.2 | 518.7 | 511.8 | 311.1 | 303.2 | 300.3 | 289.1 | 245.8 |
| | | Catalyst | Type | MPPO | MPPO | MPPO | MPPO | MPPO | MPPO | MPPO | MPPO | MPPO | MPPO |
| | | | Parts by mass | 2.0 | 2.0 | 2.0 | 2.0 | 2.0 | 2.0 | 2.0 | 2.0 | 2.0 | 2.0 |
| | Reaction conditions | Reaction temperature | °C. | 128 | 150 | 141 | 150 | 125 | 141 | 141 | 150 | 150 | 141 |
| | | Reaction time | Hours | 12 | 7 | 5 | 10 | 16 | 8 | 3 | 10 | 12 | 8.5 |
| (Second) Urethane-formation step | Mixing formulation | Other alcohol | Type | None | None | None | None | None | None | None | None | None | None |
| | | | Parts by mass | | | | | | | | | | |
| | Reaction conditions | Reaction temperature | °C. | | | | | | | | | | |
| | | Reaction time | Hours | | | | | | | | | | |
| Analysis | | Equivalent ratio $R_{Total}$(NCO/OH) | | 7.0 | 7.0 | 7.0 | 15.0 | 16.0 | 7.0 | 7.0 | 7.0 | 7.0 | 7.0 |
| | | Alcohol containing three or more consecutive oxyethylene groups/Total alcohol amount(mol %) | | 42 | 42 | 42 | 50 | 50 | 42 | 44 | 44 | 44 | 0 |
| | | Three or more consecutive oxyethylene groups/Polycarbodiimide composition(mass %) | | 27.4 | 27.4 | 27.4 | 18.1 | 14.3 | 25.8 | 24.8 | 24.2 | 22.0 | 0.0 |
| | | Carbodiimide/ (Uretonimine + Urethane) | IR intensity ratio | 2.2 | 2.9 | 2.7 | 4.4 | 1.6 | 2.7 | 2.5 | 3.2 | 3.4 | 2.3 |
| | | Uretonimine/ (Carbodiimide + Uretonimine) | mol % | 11.3 | 3.9 | 6.2 | 1.3 | 15.6 | 5.8 | 5.6 | 4.9 | 4.5 | 7.1 |
| Evaluation | | Flowability | | 3 | 3 | 3 | 2 | 2 | 3 | 2 | 2 | 2 | 3 |
| | | Water dispersiveness (80° C., 40%) | | 4 | 4 | 4 | 2 | 2 | 3 | 3 | 3 | 3 | — |
| | Coating 80° C. | Coating properties | | 3 | 3 | 3 | 1 | 1 | 3 | 3 | 3 | 3 | 3 |
| | | Water resistant characteristics | | 4 | 4 | 4 | 4 | 4 | 3 | 4 | 4 | 4 | 4 |
| | | Chemical resistance (10 minutes) | | 4 | 4 | 4 | 4 | 3 | 3 | 4 | 3 | 2 | 4 |
| | | Chemical resistance (30 minutes) | | 4 | 4 | 4 | 4 | 4 | 4 | 4 | 3 | 3 | 4 |

TABLE 3

| | | | | No. Example 21 | No. Example 22 |
|---|---|---|---|---|---|
| (First) Urethane-formation step | Mixing formulation | Polyisocyanate 1 | Type | PDI | PDI |
| | | | Parts by mass | 100 | 100 |
| | | Alcohol containing three or more consecutive oxyethylene groups | Type | Uniox M550 | Uniox M550 |
| | | | Parts by mass | 0.0 | 0.0 |
| | | Other alcohol | Type | 1-methoxy-2-propanol | 1-methoxy-2-propanol |
| | | | Parts by mass | 0.0 | 10.8 |
| | Reaction conditions | Reaction temperature | °C. | — | 80 |
| | | Reaction time | Hours | — | 6 |
| | Mixing formulation | Polyisocyanate 2 | Type | H6XDI | H6XDI |
| | | | Parts by mass | 42 | 42 |
| | | Alcohol containing three or more consecutive oxyethylene groups | Type | Uniox M550 | Uniox M550 |
| | | | Parts by mass | 52.9 | 52.9 |
| | | Other alcohol | Type | 1-methoxy-2-propanol | 1-methoxy-2-propanol |
| | | | Parts by mass | 10.8 | 0.0 |
| | Reaction conditions | Reaction temperature | °C. | 80 | 80 |
| | | Reaction time | Hours | 7 | 7 |
| Carbodiimide-formation step | Mixing formulation | Organic solvent | Type | PMA | PMA |
| | | | Parts by mass | 431.8 | 431.8 |
| | | Catalyst | Type | MPPO | MPPO |
| | | | Parts by mass | 2.8 | 2.8 |
| | Reaction conditions | Reaction temperature | °C. | 150 | 150 |
| | | Reaction time | Hours | 9 | 9 |
| Analysis | | Equivalent ratio $R_{Total}$(NCO/OH) | | 8.0 | 8.0 |
| | | Alcohol containing three or more consecutive oxyethylene groups/Total alcohol amount(mol %) | | 44 | 44 |
| | | Three or more consecutive oxyethylene groups/Polycarbodiimide composition(mass %) | | 25.0 | 25.0 |
| | | Carbodiimide/(Uretonimine + Urethane) IR intensity ratio | | 3.2 | 3.1 |
| | | Uretonimine/(Carbodiimide + Uretonimine) mol % | | 5.5 | 5.0 |
| Evaluation | | Flowability | | 3 | 3 |
| | | Water dispersiveness (80° C., 40%) | | 4 | 4 |
| | Coating 80° C. | Coating properties | | 3 | 3 |
| | | Water resistant characteristics | | 4 | 4 |
| | | Chemical resistance (10 minutes) | | 3 | 3 |
| | | Chemical resistance (30 minutes) | | 4 | 4 |

TABLE 4

| No. | | | | Comparative Example 1 | Comparative Example 2 | Comparative Example 3 | Comparative Example 4 | Comparative Example 5 | Comparative Example 6 |
|---|---|---|---|---|---|---|---|---|---|
| (First) Urethane-formation step | Mixing formulation | Polyisocyanate | Type | PDI | PDI | PDI | PDI | HDI | HDI |
| | | | Parts by mass | 100 | 100 | 100 | 100 | 673 | 100 |
| | | Alcohol containing three or more consecutive oxyethylene groups | Type | Uniox M550 | Uniox M550 | Uniox M400 | Uniox M550 | Uniox M400 | Uniox M550 |
| | | | Parts by mass | 118.9 | 17.8 | 43.0 | 43.0 | 800 | 39.4 |
| | | Other alcohol | Type | 1-methoxy-2-propanol | 1-methoxy-2-propanol | 1-methoxy-2-propanol | 1-methoxy-2-propanol | — | 1-methoxy-2-propanol |
| | | | Parts by mass | 39.0 | 2.92 | 9.7 | 9.7 | — | 8.9 |
| | Reaction conditions | Reaction temperature | °C. | 80 | 80 | 80 | 80 | 120 | 80 |
| | | Reaction time | Hours | 6 | 6 | 6 | 6 | 1 | 6 |
| Carbodiimide-formation step | Mixing formulation | Organic solvent | Type | Xylene | PMA | Toluene | Tetralin | — | Xylene |
| | | | Parts by mass | 538.2 | 491.1 | 320.2 | 320.2 | — | 311.1 |
| | | Catalyst | Type | MPPO | MPPO | MPPO | MPPO | MPPO | EMPO |
| | | | Parts by mass | 2.0 | 2.0 | 2.0 | 2.0 | 13.5 | 2.0 |
| | Reaction conditions | Reaction temperature | °C. | 141 | 150 | 115 | 195 | 185 | 80 120 |
| | | Reaction time | Hours | 7 | 11 | Solidified after 20 hours | Solidified after 4 hours | Solidified after 2 hours | 2 Solidified after 14 hours |

TABLE 4-continued

| No. | | | | Comparative Example 1 | Comparative Example 2 | Comparative Example 3 | Comparative Example 4 | Comparative Example 5 | Comparative Example 6 |
|---|---|---|---|---|---|---|---|---|---|
| (Second) Urethane-formation step | Mixing formulation | Other alcohol | Type Parts by mass | None | None | None | None | — — | None |
| | Reaction conditions | Reaction temperature | ° C. | | | | | — | |
| | | Reaction time | Hours | | | | | — | |
| Analysis | Equivalent ratio $R_{Total}$(NCO/OH) | | | 2.0 | 20.2 | 7.0 | 7.0 | 6.0 | 7.0 |
| | Alcohol containing three or more consecutive oxyethylene groups/ Total alcohol amount(mol %) | | | 33 | 50 | 42 | 42 | 100 | 42.0 |
| | Three or more consecutive oxyethylene groups/Polycarbodiimide composition(mass %) | | | 44.9 | 14.3 | 27.4 | 27.4 | 52.3 | 25.8 |
| | Carbodiimide/ (Uretonimine + Urethane) | | IR intensity ratio | 1.2 | 5.3 | 0.8 | 1.4 | 1.3 | 0.8 |
| | Uretonimine/ (Carbodiimide + Uretonimine) | | mol % | 8.0 | 0.7 | 39.2 | 12.5 | 21.3 | 34.9 |
| Evaluation | Flowability | | | 3 | 1 | 1 | 1 | 1 | 1 |
| | Water dispersiveness (80° C., 40%) | | | 3 | 1 | 1 | 1 | 1 | 1 |
| | Coating 80° C. | Coating properties | | 3 | — | — | — | — | — |
| | | Water resistant characteristics | | 1 | — | — | — | — | — |
| | | Chemical resistance (10 minutes) | | 1 | — | — | — | — | — |
| | | Chemical resistance (30 minutes) | | 1 | — | — | — | — | — |

<Consideration>

The resin composition of the Comparative Example 1 has a low IR intensity ratio ($IR_{CI}/IR_{UI+U}$), and has excellent water dispersiveness and coating properties, but water resistance and chemical resistance properties of the coating are poor.

In contrast, the resin composition of Comparative Example 2 has a high IR intensity ratio ($IR_{CI}/IR_{UI+U}$), and even though it contains UNIOXM550 (that is, alcohol containing three or more consecutive oxyethylene groups) and contains sufficient hydrophilic groups, water dispersiveness is poor and could not be used.

When reaction temperature in carbodiimide-formation reaction is excessively high, as in Comparative Examples 3 to 4, the resin composition solidifies, the IR intensity ratio ($IR_{CI}/IR_{UI+U}$) is low, and the proportion of the uretonimine group relative to a total mol of the carbodiimide group and the uretonimine group is high.

When the reaction temperature in carbodiimide-formation reaction is excessively low as well, as in Comparative Example 5, the resin composition solidifies, the IR intensity ratio ($IR_{CI}/IR_{UI+U}$) is low, and the proportion of the uretonimine group relative to a total mol of the carbodiimide group and the uretonimine group is high.

While the illustrative embodiments of the present invention are provided in the above description, such is for illustrative purpose only and it is not to be construed as limiting in any manner. Modification and variation of the present invention that will be obvious to those skilled in the art is to be covered by the following claims.

INDUSTRIAL APPLICABILITY

The polycarbodiimide composition, method for producing a polycarbodiimide composition, aqueous dispersion composition, solution composition, resin composition, and cured resin of the present invention are suitably used in various fields such as, for example, coating material, adhesive material (adhesive), pressure-sensitive adhesive material (pressure-sensitive adhesive), ink, sealant, molding material, foam and optical material, and also resin modifier that modifies resin such as polyester, polylactic acid, polyamide, and polyimide.

The invention claimed is:

1. A polycarbodiimide composition comprising:
   a reaction product of polyisocyanate having a primary isocyanate group and alcohols,
   wherein the polycarbodiimide composition includes a carbodiimide group and a uretonimine group,
   in an infrared absorption spectrum, the intensity ratio ($IR_{CI}/IR_{UI+U}$) of absorbance $IR_{CI}$ at or near 2120 cm$^{-1}$ due to stretching vibration of the carbodiimide group relative to absorbance $IR_{UI+U}$ at or near 1720 cm$^{-1}$ due to stretching vibration of the uretonimine group and urethane group is 1.5 or more and 4.5 or less, and
   the equivalent ratio (NCO/OH) of the isocyanate group of polyisocyanate relative to the hydroxyl group of the alcohols is more than 2 and 16 or less.

2. The polycarbodiimide composition according to claim 1, wherein in the polycarbodiimide composition, the proportion of the uretonimine group relative to a total mol of the carbodiimide group and the uretonimine group is 1.5 mol % or more and 15 mol % or less.

3. The polycarbodiimide composition according to claim 1, wherein the alcohols contain an alcohol containing three or more consecutive oxyethylene groups, and 10 mass % or more and 40 mass % or less of the three or more consecutive oxyethylene groups is contained relative to the polycarbodiimide composition.

4. The polycarbodiimide composition according to claim 1, wherein the alcohols contain an alcohol containing three or more consecutive oxyethylene groups, and 5 mol % or more and 50 mol % or less of the alcohol containing three or more consecutive oxyethylene groups is contained relative to a total mol of the alcohols.

5. The polycarbodiimide composition according to claim 1, wherein the polyisocyanate is aliphatic polyisocyanate.

6. The polycarbodiimide composition according to claim 5, wherein the aliphatic polyisocyanate is pentamethylene diisocyanate.

7. A method for producing the polycarbodiimide composition according to claim 1, the method comprising the steps of:
- a urethane-formation step, in which the polyisocyanate and the alcohols are subjected to urethane-forming reaction, and
- a carbodiimide-formation step, in which the reaction product of the urethane-formation step is heated in the presence of a carbodiimide-formation catalyst to cause carbodiimide-formation reaction.

8. The method for producing a polycarbodiimide composition according to claim 7, wherein the reaction temperature in the carbodiimide-formation reaction is 125° C. or more and 160° C. or less.

9. The method for producing a polycarbodiimide composition according to claim 7, wherein the carbodiimide-formation reaction is performed while refluxing.

10. An aqueous dispersion composition, wherein the aqueous dispersion composition is an aqueous dispersion in which the polycarbodiimide composition according to claim 1 is dispersed in water at a ratio of a solid content concentration of 5 mass % or more and 90 mass % or less.

11. A solution composition, wherein the solution composition is a solution in which the polycarbodiimide composition according to claim 1 is dissolved in an organic solvent at a ratio of a solid content concentration of 5 mass % or more and 90 mass % or less.

12. A resin composition comprising a base component having a carboxyl group, and a curing agent including the polycarbodiimide composition according to claim 1.

13. A cured resin, wherein the cured resin is a cured product of the resin composition according to claim 12.

* * * * *